United States Patent
Westrich et al.

(10) Patent No.: US 12,237,068 B2
(45) Date of Patent: *Feb. 25, 2025

(54) PREDICTING IMPLANT SIZE IN ARTHROPLASTY USING DEMOGRAPHIC VARIABLES

(71) Applicant: New York Society for the Relief of the Ruptured and Crippled, maintaining the Hospital for Special Surgery, New York, NY (US)

(72) Inventors: Geoffrey Westrich, New York, NY (US); Jason Blevins, New York, NY (US); Yu-fen Chiu, New York, NY (US); Stephen Lyman, New York, NY (US); Daniel J. Westrich, New York, NY (US)

(73) Assignee: NEW YORK SOCIETY FOR THE RELIEF OF THE RUPTURED AND CRIPPLED, MAINTAINING THE HOSPITAL FOR SPECIAL SURGERY, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/400,858

(22) Filed: Dec. 29, 2023

(65) Prior Publication Data
US 2024/0136046 A1    Apr. 25, 2024

Related U.S. Application Data

(63) Continuation of application No. 17/683,618, filed on Mar. 1, 2022, now Pat. No. 11,887,718.
(Continued)

(51) Int. Cl.
*G16H 20/40* (2018.01)
*A61B 34/00* (2016.01)
*A61B 34/10* (2016.01)

(52) U.S. Cl.
CPC ............ *G16H 20/40* (2018.01); *A61B 34/10* (2016.02); *A61B 34/25* (2016.02); *A61B 2034/102* (2016.02)

(58) Field of Classification Search
USPC ........................................................ 705/2, 3
See application file for complete search history.

(56) References Cited

U.S. PATENT DOCUMENTS 10,102,309 B2 * 10/2018 McKinnon ............. A61B 34/10
10,748,115 B2 *  8/2020 Laster .................... G16H 50/30
(Continued)

OTHER PUBLICATIONS

Evan M. Polce et al., "Machine Learning Predicts Femoral and Tibial Implant Size Mismatch for Total Knee Arthroplasty", Arthroplasty Today, Feb. 2021, pp. 268-277.
(Continued)

*Primary Examiner* — Ishrat I Sherali
(74) *Attorney, Agent, or Firm* — Leason Ellis LLP

(57) ABSTRACT

In one or more implementations, a method and system are disclosed in which at least one processor receives information associated with an upcoming arthroplasty and demographic factors of a patient in the upcoming arthroplasty. The processor(s) access i) procedure information representing arthroplasty previously performed for each of a plurality of patients and ii) implant information representing types and sizes of implants from a plurality of manufacturers. Further, the processor(s) determine respective unadjusted probabilities of each of a plurality of implant size options within a range of implant sizes, based on i) of at least one statistical model, ii) the accessed procedure information and the implant information, and iii) the demographic factors of the patient. Moreover, the processor(s) generate information representing some of the respective implant size options and unadjusted probabilities and transmits automatically, to at
(Continued)

least one computing device associated with an inventory control system, the generated information.

20 Claims, 12 Drawing Sheets

Related U.S. Application Data

(60) Provisional application No. 63/155,106, filed on Mar. 1, 2021, provisional application No. 63/194,450, filed on May 28, 2021, provisional application No. 63/195,095, filed on May 31, 2021.

(56) References Cited

U.S. PATENT DOCUMENTS

| | | | | |
|---|---|---|---|---|
| 10,849,689 | B1* | 12/2020 | Hu | G16H 20/40 |
| 11,684,423 | B2* | 6/2023 | McKinnon | G16H 15/00 |
| | | | | 703/11 |
| 11,887,718 | B2* | 1/2024 | Westrich | G16H 50/50 |
| 2007/0233267 | A1 | 10/2007 | Amirouche et al. | |
| 2011/0295887 | A1* | 12/2011 | Palmese | G16H 20/40 |
| | | | | 707/769 |
| 2012/0226198 | A1* | 9/2012 | Carson | A61B 90/36 |
| | | | | 600/587 |
| 2016/0220323 | A1 | 8/2016 | Forrest et al. | |
| 2018/0330800 | A1 | 11/2018 | Bogue et al. | |
| 2019/0015213 | A1 | 1/2019 | Mahfouz | |
| 2019/0073632 | A1 | 3/2019 | Laster et al. | |
| 2019/0325386 | A1 | 10/2019 | Laster et al. | |
| 2019/0388153 | A1 | 12/2019 | Running et al. | |
| 2020/0275976 | A1 | 9/2020 | Mckinnon et al. | |
| 2020/0323649 | A1 | 10/2020 | Schippeer et al. | |
| 2022/0093232 | A1 | 3/2022 | Wirth et al. | |

OTHER PUBLICATIONS

Stephen J. Wallace et al., "Demographic data is more predictive of component size than digital radiographic templating in total knee arthroplasty", Knee Surgery & Related Research, Nov. 2000 (7 pages).

Jason L. Blevins et al., "Predicting implant size in total knee arthroplasty using demographic variables: linear regression and Bayesian modelling", The bone & joint journal, Jun. 2020.

International Search Report and Written Opinion mailed on May 16, 2022 (10 pages).

Steven M. Kurts et al., "Future young patient demand for primary and revision joint replacement: national projections from 2010 to 2030", Clin Orthop Relat Res. Apr. 2009, pp. 2606-2612.

Alexander S. McLawhorn et al., Abstract—"Template-Directed Instrumentation Reduces Cost and Improves Efficiency for Total Knee Arthroplasty: An Economic Decision Analysis and Pilot Study", J Arthroplasty. Oct. 2015, pp. 1699-1704.

Rorbert A. Sershon MD et al., Abstract—"Can Demographic Variables Accurately Predict Component Sizing in Primary Total Knee Arthroplasty?", Oct. 2017, pp. 3004-3008.

Bayes et al., "An essay towards solving a problem in the doctrine of chances.", By the late Rev. Mr. Bayes, FRS communicated by Mr. Price, in a letter to John Canton, Amfr S. Philosophical transactions of the Royal Society of London. Dec. 1763, pp. 370-418.

Stephan Lyman et al., Abstract—"Surgical decision making for arthroscopic partial meniscectomy in patients aged over 40 years", Arthroscopy. Apr. 2012, pp. 492-501.

No authors listed. Global Database on Body Mass Index. World Health Organization. http://www.euro.who.int/en/health-topics/disease-prevention/nutrition/a-healthy-lifestyle/body-mass-index-bmi (date last accessed Apr. 21, 2020).

Matthew P. Abdel MD, Abstract—"Increased Aseptic Tibial Failures in Patients With a BMI 35 and Well-Aligned Total Knee Arthroplasties", J Arthroplasty. Dec. 2015, pp. 2181-2184.

Michael E. Berend MD et al.,—Abstract "Implant migration and failure in total knee arthroplasty is related to body mass index and tibial component size", J Arthroplasty. Sep. 2008, pp. 104-109.

Thomas K. Fehring MD et al.,—Abstract "Catastrophic Varus Collapse of the Tibia in Obese Total Knee Arthroplasty". J Arthroplasty. May 2017, p. 1625-1629.

J. Ryan Martin Md et al.—Abstract "Radiographic Findings in Patients With Catastrophic Varus Collapse After Total Knee Arthroplasty". J Arthroplasty. Jan. 2018, pp. 241-244.

Matthew G. Prohaska, MD et al., Preoperative body mass index and physical function are associated with length of stay and facility discharge after total knee arthroplasty:, Knee. Jun. 2017, pp. 634-640.

Extended European Search Report in EP Application No. 22763870.7-1122/4302310, mailed Dec. 23, 2024 (10 pages).

* cited by examiner

FIG. 4A

| Scenarios | | | Stem AP (mm) | | | | | | | |
|---|---|---|---|---|---|---|---|---|---|---|
| Sex | Weight (kg) | Height (cm) | 12-14 | 14-16 | 16-18 | 18-20 | 20-22 | 22-24 | 24-26 | 26-28 |
| Male | <50 | <150 | 46.8% | 20.5% | 15.6% | 15.0% | 2.1% | 0.0% | 0.0% | 0.0% |
| Male | <50 | 150-155 | 47.9% | 19.8% | 15.7% | 13.9% | 2.8% | 0.0% | 0.0% | 0.0% |
| Male | <50 | 155-160 | 46.6% | 20.7% | 17.1% | 11.2% | 4.4% | 0.0% | 0.0% | 0.0% |
| Male | <50 | 160-165 | 41.7% | 22.8% | 16.1% | 14.4% | 5.0% | 0.0% | 0.0% | 0.0% |
| Male | <50 | 165-170 | 37.0% | 20.3% | 18.3% | 17.1% | 7.3% | 0.0% | 0.0% | 0.0% |
| Male | <50 | 170-175 | 34.9% | 18.4% | 18.5% | 18.6% | 9.6% | 0.0% | 0.0% | 0.0% |
| Male | <50 | 175-180 | 32.3% | 13.9% | 19.5% | 19.7% | 14.6% | 0.0% | 0.0% | 0.0% |
| Male | <50 | 180-185 | 28.0% | 11.7% | 19.3% | 23.5% | 17.6% | 0.0% | 0.0% | 0.0% |
| Male | <50 | 185-190 | 29.0% | 9.2% | 20.3% | 23.8% | 17.7% | 0.0% | 0.0% | 0.0% |
| Male | <50 | >=190 | 30.1% | 3.3% | 13.3% | 25.1% | 28.2% | 0.0% | 0.0% | 0.0% |
| Male | 50-60 | <150 | 44.5% | 16.9% | 22.7% | 13.2% | 2.3% | 0.5% | 0.0% | 0.0% |
| Male | 50-60 | 150-155 | 45.5% | 16.3% | 22.9% | 12.2% | 3.1% | 0.0% | 0.0% | 0.0% |
| Male | 50-60 | 155-160 | 43.9% | 16.9% | 24.7% | 9.7% | 4.8% | 0.1% | 0.0% | 0.0% |
| Male | 50-60 | 160-165 | 39.6% | 18.7% | 23.5% | 12.6% | 5.5% | 0.1% | 0.0% | 0.0% |
| Male | 50-60 | 165-170 | 34.4% | 16.4% | 26.1% | 14.7% | 7.8% | 0.6% | 0.0% | 0.0% |
| Male | 50-60 | 170-175 | 31.9% | 14.6% | 26.1% | 15.7% | 10.2% | 1.5% | 0.0% | 0.0% |
| Male | 50-60 | 175-180 | 29.2% | 10.9% | 27.0% | 16.4% | 15.3% | 1.3% | 0.0% | 0.0% |
| Male | 50-60 | 180-185 | 24.9% | 9.0% | 26.3% | 19.3% | 18.1% | 2.4% | 0.0% | 0.0% |
| Male | 50-60 | 185-190 | 25.1% | 6.9% | 27.1% | 19.1% | 17.8% | 4.1% | 0.0% | 0.0% |
| Male | 50-60 | >=190 | 26.0% | 2.4% | 17.7% | 20.0% | 28.3% | 5.7% | 0.0% | 0.0% |
| Male | 60-70 | <150 | 43.7% | 15.2% | 21.0% | 13.8% | 3.3% | 3.0% | 0.0% | 0.0% |
| Male | 60-70 | 150-155 | 43.7% | 15.0% | 21.7% | 13.1% | 4.5% | 0.0% | 0.0% | 0.0% |
| Male | 60-70 | 155-160 | 43.6% | 15.4% | 23.1% | 10.3% | 6.9% | 0.6% | 0.0% | 0.0% |
| Male | 60-70 | 160-165 | 39.1% | 17.0% | 21.8% | 13.4% | 7.9% | 0.6% | 0.2% | 0.0% |
| Male | 60-70 | 165-170 | 32.7% | 14.3% | 23.4% | 15.0% | 10.8% | 3.6% | 0.2% | 0.0% |
| Male | 60-70 | 170-175 | 28.5% | 12.1% | 22.0% | 15.0% | 13.3% | 8.6% | 0.3% | 0.0% |
| Male | 60-70 | 175-180 | 25.5% | 8.7% | 22.2% | 15.3% | 19.4% | 7.1% | 1.6% | 0.0% |
| Male | 60-70 | 180-185 | 20.2% | 6.7% | 20.1% | 16.7% | 21.3% | 12.2% | 2.7% | 0.0% |
| Male | 60-70 | 185-190 | 19.1% | 4.8% | 19.4% | 15.5% | 19.7% | 19.5% | 1.9% | 0.0% |
| Male | 60-70 | >=190 | 16.6% | 1.4% | 10.7% | 13.7% | 26.3% | 23.0% | 8.3% | 0.0% |
| Male | 70-80 | <150 | 33.7% | 14.3% | 24.6% | 14.5% | 4.6% | 8.4% | 0.0% | 0.0% |
| Male | 70-80 | 150-155 | 37.2% | 14.9% | 26.8% | 14.5% | 6.6% | 0.0% | 0.0% | 0.0% |

FIG. 4B

| Scenarios | | | Stem ML (mm) | | | | | | | | | |
|---|---|---|---|---|---|---|---|---|---|---|---|---|
| Sex | Weight (kg) | Height (cm) | 22-24 | 24-26 | 26-28 | 28-30 | 30-32 | 32-34 | 34-36 | 36-38 | 38-40 | 40-42 |
| Male | <50 | <150 | 2.2% | 4.6% | 15.1% | | 23.0% | 1.9% | 0.2% | 0.0% | 0.0% | 0.0% |
| Male | <50 | 150-155 | 1.2% | 5.1% | 11.3% | | 25.2% | 1.5% | 0.0% | 0.0% | 0.0% | 0.0% |
| Male | <50 | 155-160 | 0.5% | 4.7% | 10.5% | | 26.5% | 3.6% | 0.2% | 0.0% | 0.0% | 0.0% |
| Male | <50 | 160-165 | 0.5% | 3.5% | 9.1% | | 3.8% | 3.5% | 0.2% | 0.0% | 0.0% | 0.0% |
| Male | <50 | 165-170 | 0.3% | 1.8% | 6.2% | .1% | .3% | 6.8% | 0.6% | 0.0% | 0.0% | 0.0% |
| Male | <50 | 170-175 | 0.2% | 1.0% | 2.4% | 6.2% | 6.6% | 12.1% | 1.6% | 0.0% | 0.0% | 0.0% |
| Male | <50 | 175-180 | 0.0% | 0.4% | 2.2% | 22.7% | 2% | 20.5% | 3.0% | 0.0% | 0.0% | 0.0% |
| Male | <50 | 180-185 | 0.0% | 0.0% | 1.2% | 17.9% | 2% | 28.1% | 5.7% | 0.0% | 0.0% | 0.0% |
| Male | <50 | 185-190 | 0.2% | 0.2% | 0.8% | 11.9% | 4% | 27.3% | 9.2% | 0.0% | 0.0% | 0.0% |
| Male | >=190 | | 0.0% | 1.4% | 0.0% | 5.6% | .8% | 0.4% | 19.8% | 0.0% | 0.0% | 0.0% |
| Male | 50-60 | <150 | 1.4% | 3.8% | 14.2% | 0% | 29.1% | 4.3% | 0.2% | 0.0% | 0.0% | 0.0% |
| Male | 50-60 | 150-155 | 0.8% | 4.1% | 10.6% | 3% | 1.9% | 3.3% | 0.0% | 0.0% | 0.0% | 0.0% |
| Male | 50-60 | 155-160 | 0.3% | 3.7% | 9.5% | 9% | 2.3% | 8.0% | 0.2% | 0.0% | 0.0% | 0.0% |
| Male | 50-60 | 160-165 | 0.3% | 2.7% | 8.1% | .2% | .2% | 7.4% | 0.2% | 0.0% | 0.0% | 0.0% |
| Male | 50-60 | 165-170 | 0.2% | 1.3% | 5.1% | 3.4% | 9% | 13.6% | 0.5% | 0.0% | 0.0% | 0.0% |
| Male | 50-60 | 170-175 | 0.1% | 0.6% | 1.8% | 25.9% | 8% | 22.3% | 1.4% | 0.0% | 0.0% | 0.0% |
| Male | 50-60 | 175-180 | 0.0% | 0.2% | 1.5% | 14.6% | 1% | 4.1% | 2.4% | 0.0% | 0.0% | 0.0% |
| Male | 50-60 | 180-185 | 0.0% | 0.0% | 0.8% | 10.8% | 6% | 6% | 4.3% | 0.0% | 0.0% | 0.0% |
| Male | 50-60 | 185-190 | 0.1% | 0.1% | 0.5% | 7.1% | .1% | .2% | 6.8% | 0.0% | 0.0% | 0.0% |
| Male | 50-60 | >=190 | 0.0% | 0.8% | 0.0% | 3.3% | .8% | .8% | 14.3% | 0.0% | 0.0% | 0.0% |
| Male | 60-70 | <150 | 1.2% | 2.6% | 10.9% | 9% | 2.1% | 5.6% | 0.6% | 0.0% | 0.2% | 0.0% |
| Male | 60-70 | 150-155 | 0.6% | 2.8% | 8.2% | 9% | 5.1% | 4.3% | 0.0% | 0.2% | 0.0% | 0.0% |
| Male | 60-70 | 155-160 | 0.3% | 2.4% | 7.1% | .5% | 4.7% | 10.1% | 0.6% | 0.3% | 0.0% | 0.0% |
| Male | 60-70 | 160-165 | 0.2% | 1.8% | 6.0% | .4% | .6% | 9.3% | 0.5% | 0.3% | 0.0% | 0.0% |
| Male | 60-70 | 165-170 | 0.1% | 0.8% | 3.6% | 30.7% | 7% | 16.3% | 1.4% | 0.4% | 0.0% | 0.0% |
| Male | 60-70 | 170-175 | 0.1% | 0.4% | 1.2% | 22.6% | 2% | 25.5% | 3.5% | 0.4% | 0.1% | 0.0% |
| Male | 60-70 | 175-180 | 0.0% | 0.1% | 0.9% | 12.1% | 3% | 7.0% | 5.5% | 0.7% | 0.4% | 0.0% |
| Male | 60-70 | 180-185 | 0.0% | 0.0% | 0.5% | 8.4% | 5.3% | 7% | 9.3% | 1.3% | 0.6% | 0.0% |
| Male | 60-70 | 185-190 | 0.0% | 0.1% | 0.3% | 5.4% | 5.8% | .4% | 14.2% | 2.3% | 0.6% | 0.0% |
| Male | 60-70 | >=190 | 0.0% | 0.3% | 0.0% | 2.1% | 25.6% | .6% | 25.7% | 5.5% | 2.2% | 0.0% |
| Male | 70-80 | <150 | 0.4% | 1.9% | 7.9% | 7.5% | .5% | 9.3% | 1.7% | 0.0% | 1.6% | 0.0% |
| Male | 70-80 | 150-155 | 0.2% | 2.2% | 6.0% | 9.9% | .0% | 7.2% | 0.0% | 0.4% | 0.0% | 0.0% |

FIG. 4C

| Scenarios | | | Cup OD (mm) | | | | | | |
|---|---|---|---|---|---|---|---|---|---|
| Sex | Weight (kg) | Height (cm) | <42 | 42-46 | 46-50 | 50-54 | 54-58 | 58-62 | 62-66 |
| Male | <50 | <150 | 0.0% | 9.1% | ▓▓% | ▓3.2% | 1.1% | 0.0% | 0.0% |
| Male | <50 | 150-155 | 0.0% | 5.2% | ▓▓% | ▓4.4% | 1.5% | 0.0% | 0.0% |
| Male | <50 | 155-160 | 0.0% | 2.8% | ▓▓.8% | ▓.6% | 1.9% | 0.0% | 0.0% |
| Male | <50 | 160-165 | 0.0% | 1.3% | ▓6.9% | ▓▓% | 2.7% | 0.0% | 0.0% |
| Male | <50 | 165-170 | 0.0% | 0.7% | 23.6% | ▓▓ | 9.1% | 0.0% | 0.0% |
| Male | <50 | 170-175 | 0.0% | 0.3% | 10.3% | ▓▓ | 18.1% | 0.0% | 0.0% |
| Male | <50 | 175-180 | 0.0% | 0.0% | 3.2% | ▓▓% | ▓1.9% | 0.0% | 0.0% |
| Male | <50 | 180-185 | 0.0% | 0.0% | 1.0% | ▓▓% | ▓.2% | 0.0% | 0.0% |
| Male | <50 | 185-190 | 0.0% | 0.0% | 0.2% | ▓0.5% | ▓▓% | 0.0% | 0.0% |
| Male | <50 | >=190 | 0.0% | 0.0% | 2.3% | 18.2% | ▓▓ | 0.0% | 0.0% |
| Male | 50-60 | <150 | 0.0% | 4.0% | ▓▓.8% | ▓4% | 0.7% | 0.1% | 0.0% |
| Male | 50-60 | 150-155 | 0.0% | 2.2% | ▓▓.6% | ▓1% | 0.9% | 0.1% | 0.0% |
| Male | 50-60 | 155-160 | 0.0% | 1.1% | ▓5.4% | ▓▓% | 1.1% | 0.0% | 0.0% |
| Male | 50-60 | 160-165 | 0.0% | 0.5% | 24.0% | ▓▓ | 1.4% | 0.0% | 0.0% |
| Male | 50-60 | 165-170 | 0.0% | 0.2% | 14.8% | ▓▓ | 4.7% | 0.1% | 0.0% |
| Male | 50-60 | 170-175 | 0.0% | 0.1% | 6.3% | ▓▓ | 9.1% | 0.2% | 0.0% |
| Male | 50-60 | 175-180 | 0.0% | 0.0% | 2.1% | ▓▓ | 16.9% | 0.7% | 0.0% |
| Male | 50-60 | 180-185 | 0.0% | 0.0% | 0.7% | ▓▓ | 27.4% | 1.6% | 0.0% |
| Male | 50-60 | 185-190 | 0.0% | 0.0% | 0.2% | ▓▓% | ▓7.2% | 3.2% | 0.0% |
| Male | 50-60 | >=190 | 0.0% | 0.0% | 2.0% | ▓1.3% | ▓▓% | 8.3% | 0.0% |
| Male | 60-70 | <150 | 0.0% | 2.9% | ▓4.7% | ▓▓% | 2.4% | 0.3% | 0.0% |
| Male | 60-70 | 150-155 | 0.0% | 1.6% | ▓5.0% | ▓▓% | 3.1% | 0.3% | 0.0% |
| Male | 60-70 | 155-160 | 0.0% | 0.8% | ▓5.9% | ▓▓ | 3.5% | 0.2% | 0.0% |
| Male | 60-70 | 160-165 | 0.0% | 0.3% | 16.7% | ▓▓ | 4.3% | 0.2% | 0.0% |
| Male | 60-70 | 165-170 | 0.0% | 0.1% | 9.4% | ▓▓ | 12.7% | 0.3% | 0.0% |
| Male | 60-70 | 170-175 | 0.0% | 0.0% | 3.6% | ▓▓ | 22.3% | 0.7% | 0.0% |
| Male | 60-70 | 175-180 | 0.0% | 0.0% | 1.0% | ▓▓% | ▓5.9% | 2.2% | 0.0% |
| Male | 60-70 | 180-185 | 0.0% | 0.0% | 0.3% | ▓.7% | ▓.8% | 4.2% | 0.0% |
| Male | 60-70 | 185-190 | 0.0% | 0.0% | 0.1% | ▓3.6% | ▓▓% | 7.3% | 0.0% |
| Male | 60-70 | >=190 | 0.0% | 0.0% | 0.6% | 13.6% | ▓▓ | 14.6% | 0.0% |
| Male | 70-80 | <150 | 0.0% | 1.5% | 22.5% | ▓▓ | 5.9% | 1.7% | 0.0% |
| Male | 70-80 | 150-155 | 0.0% | 0.8% | 22.4% | ▓▓ | 7.6% | 1.4% | 0.0% |
| Male | 70-80 | 155-160 | 0.0% | 0.4% | 15.7% | ▓▓ | 8.1% | 0.8% | 0.0% |
| Male | 70-80 | 160-165 | 0.0% | 0.1% | 9.6% | ▓▓ | 9.5% | 0.9% | 0.0% |
| Male | 70-80 | 165-170 | 0.0% | 0.1% | 4.7% | ▓▓ | 24.8% | 1.2% | 0.0% |

FIG. 4D

PREDICTING IMPLANT SIZE IN ARTHROPLASTY USING DEMOGRAPHIC VARIABLES

CROSS-REFERENCE TO RELATED PATENT APPLICATIONS

This application is a continuation of U.S. patent application Ser. No. 17/683,618, filed Mar. 1, 2022, which claims priority to: U.S. Provisional Patent Application 63/155,106, filed Mar. 1, 2021; U.S. Provisional Patent Application 63/194,450, filed May 28, 2021; and U.S. Provisional Patent Application 63/195,095, filed May 31, 2021, each of which is incorporated by reference, as if expressly set forth in its respective entirety herein.

FIELD

The present disclosure relates, generally, to data management and communications and, more particularly, to a system and method for predicting implant size in arthroplasty procedures.

BACKGROUND

Predicting implant sizing prior to arthroplasty procedures, including total knee arthroplasty (TKA) and total hip arthroplasty (THA), can assist with optimizing the delivery of care by streamlining inventory control and related costs. Further, accurate implant size predictions can have a profound effect on efficiencies with the supply chain from various orthopedic manufacturers. Accurate implant sizing predictions can minimize the number of implants that need to be delivered to a hospital or ambulatory surgery center, and also improves space management, such as to streamline management shelf space, for one or more given cases.

More particularly, enabling a surgeon, hospital, or ambulatory care center, and/or manufacturer to predict accurately the size of a given implant, such as a knee implant for a total knee surgical procedure, direct impacts inventory requirements and significantly reduces costs including inventory costs and shipping charges, as well as storage needs and associated costs in each given case.

Unfortunately, implant sizing predictions have not been sufficiently accurate to make an impact in these and other areas. Inaccurate implant size predictions have resulted in inefficiencies in the supply chain and has not reduced requirements for resources that have to be mobilized to supply potential demand for implants of all sizes for each case.

Preoperative templating using calibrated radiographs has been shown to be an accurate means of predicting implant size, with a range of plus or minus one respective size. In addition to calibrated radiographs, femoral and tibial component size predictions have been made based on patient demographic variables and multiple logistic regression modeling. Despite an increase in accuracy resulting in such techniques, these solutions are not always adequate. The need for calibrated radiographs to allow for preoperative templating, for example, can be unavailable or otherwise impractical in clinical practice. In clinical practice, it is common for templating to not be performed until the day before or even day of surgery, which can limit the benefit for an implant manufacturer or hospital supply chain to ensure that appropriate implants are available.

The present system and method address these and other deficiencies in the art, and it is with respect to these and other considerations that the disclosure made herein is presented.

BRIEF SUMMARY

In one or more implementations, a method and system are disclosed in which at least one processor configured by executing instructions stored on processor readable media receives information associated with an upcoming arthroplasty and demographic factors of a patient in the upcoming arthroplasty. The at least one processor accesses i) procedure information representing arthroplasty previously performed for each of a plurality of patients and ii) implant information representing types and sizes of implants from a plurality of manufacturers. Further, the at least one processor determines respective unadjusted probabilities of each of a plurality of implant size options within a range of implant sizes, based on i) of at least one statistical model, ii) the accessed procedure information and the implant information, and iii) the demographic factors of the patient. Moreover, the at least one processor generates information representing some of the respective implant size options and unadjusted probabilities and transmits automatically, to at least one computing device associated with an inventory control system, the generated information.

In one or more implementations, the inventory control system generates at least one order for at least one implant respectively associated with the some of the respective implant size options and unadjusted probabilities.

In one or more implementations, the at least one processor uses at least one application programming interface ("API") to transmit the generated information to the at least one computing device associated with an inventory control system.

In one or more implementations, the at least one processor uses at least one API to transmit information associated with the generated information to at least one computing device associated with shipping, storage management, or both shipping and storage management.

In one or more implementations, the at least one processor provides, in a graphical user interface operating on at least one user computing device, information representing the respective implant size options and unadjusted probabilities. Further, the at least one processor receives, via the graphical user interface, a selection of at least one of the respective implant size options and unadjusted probabilities, wherein generating the information representing some of the respective implant size options and unadjusted probabilities is based at least in part on the selection received via the graphical user interface.

In one or more implementations, the at least one processor applies a matching algorithm to identify one unique implant size provided by each of a plurality of manufacturers, for a respective anatomical dimension size range.

In one or more implementations, the at least one statistical model is a Bayesian model.

In one or more implementations, the Bayesian model includes application of:

$$P(B) =$$

$$P(B|A_1)P(A_1) + P(B|A_2)P(A_2) + \ldots + P(B|A_n)P(A_n) = \sum_i P(B|A_i)P(A_i).$$

In one or more implementations, the patient demographics include gender, height, and weight.

In one or more implementations, the arthroplasty previously performed for each of a plurality of patients includes total knee arthroplasty or total hip arthroplasty.

Additional features, advantages, and embodiments of the disclosure may be set forth or apparent from consideration of the detailed description and drawings. It is to be understood that the foregoing summary of the disclosure and the following detailed description and drawings provide non-limiting examples that are intended to provide further explanation without limiting the scope of the disclosure as claimed.

BRIEF DESCRIPTION OF THE DRAWINGS

Aspects of the present disclosure will be more readily appreciated upon review of the detailed description of its various embodiments, described below, when taken in conjunction with the accompanying drawings, of which:

FIG. 4A illustrates example results of a testing dataset and represents the accuracy of a statistical model for predicting femoral and tibial component implant size;

FIG. 4B illustrates example results of a testing dataset and represents the accuracy of a statistical model for predicting femoral stem component implant size;

FIG. 4C illustrates example results of a testing dataset and represents the accuracy of a statistical model for predicting acetabular component implant size;

FIG. 4D illustrates example results of a testing dataset and represents the accuracy of a statistical model for predicting acetabular cup outer diameter size;

DETAILED DESCRIPTION OF CERTAIN IMPLEMENTATIONS

Figure 1:
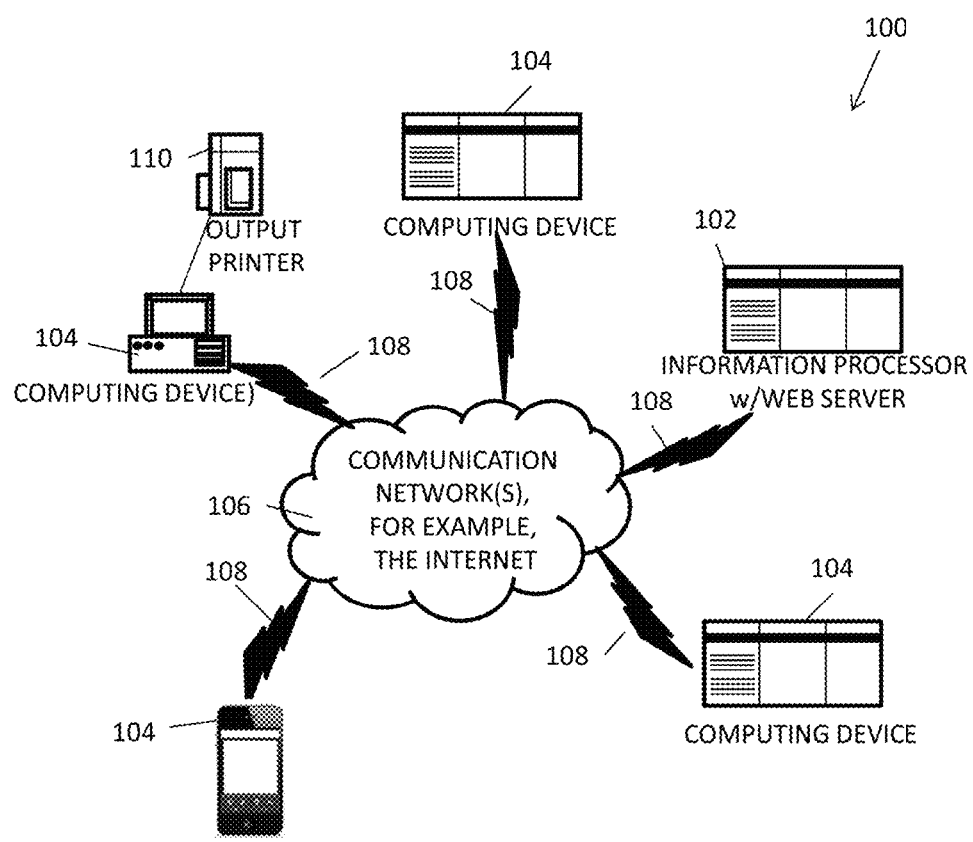
FIG. 1 is a block diagram illustrating an example implementation of the present disclosure.

By way of introduction and overview, the present disclosure provides a system and method for predicting implants and implant sizes in connection with medical procedures, such as arthroplasty. Further, the present disclosure includes systems and methods for determining corresponding percentages for each of a plurality of respective implant sizes that may effectively fit a patient. In one or more implementations of the present disclosure, various factors associated with a given patient can be received from a user and respective implants and sizes can be predicted in accordance therewith. More particularly, a relationship between a patient's height, weight, and gender can be determined and used to predict respective implant types and corresponding sizes. Additional factors can also be considered while making such predictions, including age and body mass index (BMI). Based upon one or more determined relationships between patient factors, the present disclosure supports preoperative planning in connection with predicting implant size and type, which optimizes implant inventory management and control and ensures availability for surgical cases and maximizes operating room efficiency.

As shown and described herein, respective models can be applied in the present disclosure for identification and predictive purposes. For example, one or more implementations of the present disclosure applies a multivariate linear regression model and/or a Bayesian model for predicting arthroplasty implant sizes and corresponding fit percentages. Implant sizing based on demographic variables using Bayesian modeling, for example, improves on predictive modeling for implant sizing. Such predictions and corresponding determinations configure the present disclosure to improve upon surgical planning, inventory control, facilities management and planning, as well as supply chain management and accounting for demand, including across multiple manufacturers.

In one or more implementations, the present disclosure can integrate implant and implant size prediction technology with a plurality of computing systems, user interfaces, application programming interfaces (APIs), internet web sites, and/or data sources to provide functionality not heretofore available. In one or more implementations, a database and/or and web server maintained in accordance with the present disclosure can integrate (e.g., be connected to) various user interfaces managed in accordance with the present disclosure, or third-party user interfaces and databases via one or more APIs.

In one or more implementations of the present disclosure, a user interface can be provided on a computing device that includes graphical screen controls for users to enter patient information, such as height, weight, gender, and age. Further, the user can select an implant type, such as from a particular manufacturer and/or particular model. Processing the information received in the user interface, a processor can execute instructions to predict appropriate implant sizes and percentages of likelihood of suitable fitting in accordance with the respective model. Respective implant types can be identified in accordance with stored information in a database, such as associated with respective positions that favor particular models and/or manufacturers. Moreover, the present disclosure can include instructions that, when executed by a processor, cause the processor to access manufacturer-based data sources and, as suitable, convert information to size dimensions for respective manufacturers. It is recognized by the inventors that individual healthcare providers, e.g., physicians, have particular preferences regarding implant manufacturers and models. The present disclosure supports selection of respective implants to accommodate the preferences of individual healthcare providers.

In one or more particular implementations, information associated with implants ("implant information") can be identified and categorized using data from various sources, such as one or more in-house databases, one or more third-party databases, one or more data registries, one or more patient medical records, individual chart review(s), or other data sources. Such implant information can be organized in various ways, such as by manufacturer, component size, or the like. Information, such as relating to implant size dimensions, can be obtained directly from various data sources, such as manufacturers' databases, and can include technical implant guides, descriptions, or the like. Further, information representing patient demographics, such as age, gender, height, weight, and body mass index (BMI) can be obtained from data registries and patient data sources. Once received, implant sizes (e.g., femoral and tibial implant sizes) can be converted to particular dimensions (e.g., anteroposterior (AP) dimensions and mediolateral (ML) dimensions) for each of a plurality of manufacturers. A specific algorithm can be utilized for improved comparison across different manufacturers' designs, and dimensions are chosen to represent how implants primarily increase in size on the femoral and tibial side respectively.

Referring to the drawings, in which like reference numerals refer to like elements, FIG. 1 is a block diagram illustrating an example implementation of the present disclosure and that represents an association of a plurality of devices and the flow 108 of information associated with the devices. In the example shown in FIG. 1, various computing devices 102 and 104 are shown, each capable of executing desktop and/or mobile computing device web browser application(s) including MICROSOFT EDGE, INTERNET EXPLORER, CHROME, FIREFOX, and other (e.g., SAFARI, OPERA). In addition to standard web browser application functionality, user information can be gathered via Push Notifications, and information can be retrieved from a computing device using a "REST" interface. Various mobile devices running different operating systems are shown, including IOS, ANDROID and other (e.g., PALM, WINDOWS or other mobile device) operating system.

In the example shown in FIG. 1, one or more data processing apparatuses 102 is operatively coupled to one or more user computing device(s) 104. Devices 102/104 can be respectively operated by one or more healthcare providers and associated staff, medical specialists and/or consumers. Healthcare providers can include, for example, physicians, physician assistants, nurses, therapists and/or other providers of healthcare services. Devices 102/104 can also be respectively operated by various other parties, such as implant manufacturers, inventory management sources, and scheduling systems. Data processing apparatus 102 and/or user computing device 104 can be operable to access and/or store various information on database(s) 103 including, for example, historic medical and procedure information patients, physicians, devices, or the like.

Also illustrated in FIG. 1 is a network 106, which can be configured as a local area network (LAN), wide area network (WAN), Peer-to-Peer network ("P2P"), Multi-Peer network, the Internet, one or more telephony networks or a combination thereof, that is operable to connect data processing apparatus 102 and/or devices. Though many of the examples and implementations shown and described herein relate to product and/or service recommendations, many other forms of content can be provided and/or delivered by system 100.

Figure 2:
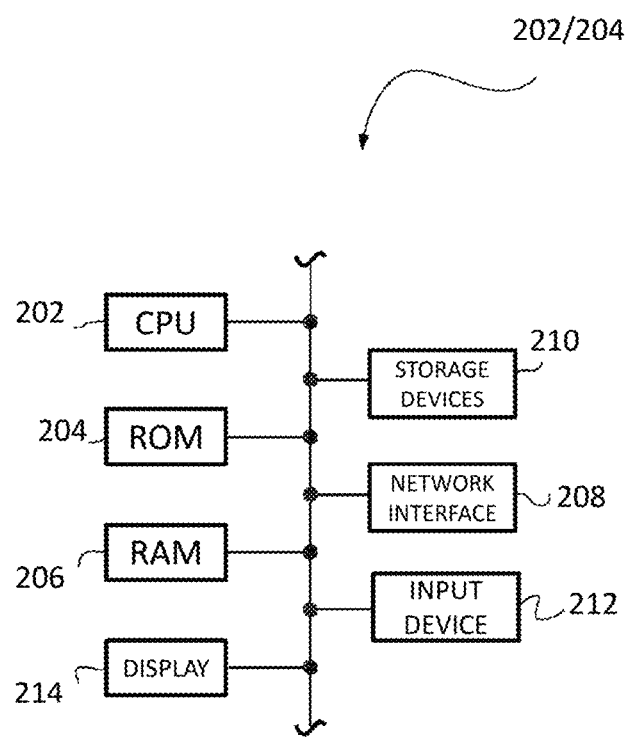
FIG. 2 is a block diagram that illustrates functional elements of one or more of data processing apparatus or computing device.

FIG. 2 is a block diagram that illustrates functional elements of one or more of data processing apparatus 102 or computing device 104 and preferably include one or more central processing units (CPU) 202 used to execute software code in order to control operations, including of data processing apparatus 102, read only memory (ROM) 204, random access memory (RAM) 206, one or more network interfaces 208 to transmit and receive data to and from other computing devices across a communication network, storage devices 210 such as a hard disk drive, solid state drive, floppy disk drive, tape drive, CD-ROM or DVD drive for storing program code, databases and application code, one or more input devices 212 such as a keyboard, mouse, track ball and the like, and a display 214.

The various components of devices 102 and/or 104 need not be physically contained within the same chassis or even located in a single location. For example, storage device 210 can be located at a site which is remote from the remaining elements of computing devices 102 and/or 104 and can even be connected to CPU 202 across communication network 106 via network interface 208.

The functional elements shown in FIG. 2 (designated by reference numbers 202-214) are preferably of the same categories of functional elements preferably present in computing device 102 and/or 104. However, not all elements need be present, for example, storage devices in the case of mobile computing devices (e.g., smartphones), and the capacities of the various elements are arranged to accommodate expected user demand. For example, CPU 202 in computing device 104 can be of a smaller capacity than CPU 202 as present in data processing apparatus 102. Similarly, it is likely that data processing apparatus 102 will include storage devices 210 of a much higher capacity than storage devices 210 present in computing device 104. Of course, one of ordinary skill in the art will understand that the capacities of the functional elements can be adjusted as needed.

The nature of the present disclosure is such that one skilled in the art of writing computer executed code (software) can implement the described functions using one or more or a combination of a popular computer programming language including but not limited to C++, JAVA, ACTIVEX, HTML, XML, ASP, SOAP, IOS, OBJECTIVE C, ANDROID, TORR and various web application development environments.

As used herein, references to displaying data on computing device 104 refer to the process of communicating data to the computing device 104 across communication network 106 and processing the data such that the data can be viewed on the user computing device 104 display 214 using a web browser, custom application or the like. The display screens on computing devices 102/104 present areas within system 100 such that a user can proceed from area to area within the system 100 by selecting a desired link. Therefore, each user's experience with system 100 will be based on the order with which (s)he progresses through the display screens. In other words, because the system is not completely hierarchical in its arrangement of display screens, users can proceed from area to area without the need to "backtrack" through a series of display screens. For that reason and unless stated otherwise, the following discussion is not intended to represent any sequential operation steps, but rather the discussion of the components of system 100.

Although the present disclosure is described by way of example herein in terms of a web-based system using web browsers, custom applications and a web site server (data processing apparatus 102), and with mobile computing devices, system 100 is not limited to that particular configuration. It is contemplated that system 100 can be arranged such that computing device 104 can communicate with, and display data received from, data processing apparatus 102 using any known communication and display method, for example, using a non-Internet browser Windows viewer coupled with a local area network protocol such as the Internetwork Packet Exchange (IPX). It is further contemplated that any suitable operating system can be used on computing device 104, for example, WINDOWS, MAC OS, OSX, LINUX, IOS, ANDROID and any suitable PDA or other computer operating system.

As used herein, the terms "function" or "module" refer to hardware, firmware, or software in combination with hardware and/or firmware for implementing features described herein. In the hardware sense, a module can be a functional hardware unit designed for use with other components or modules. For example, a module may be implemented using discrete electronic components, or it can form a portion of an entire electronic circuit such as an Application Specific Integrated Circuit (ASIC). Numerous other possibilities exist, and those of ordinary skill in the art will appreciate that the system can also be implemented as a combination of hardware and software modules. In the software sense, a module may be implemented as logic executing in a collection of software instructions, possibly having entry and exit points, written in a programming language, such as, for example, Java, Lua, C or C++. A software module may be compiled and linked into an executable program, installed in a dynamic link library, or may be written in an interpreted programming language such as, for example, Perl, or Python. It will be appreciated that software modules may be callable from other modules or from themselves, and/or may be invoked in response to detected events or interrupts. Software instructions may be embedded in firmware. Moreover, the modules described herein can be implemented as software modules, but may be represented in hardware or firmware. Generally, the modules described herein refer to logical modules that may be combined with other modules or divided into sub-modules despite their physical organization or storage.

In one or more specific implementations of the present disclosure, use of the following Bayesian theorem is employed to compute and update probabilities after obtaining new data:

$$P(B) = P(B \mid A_1)P(A_1) + P(B \mid A_2)P(A_2) + \cdots + P(B \mid A_n)P(A_n) = \sum_i P(B \mid A_i)P(A_i)$$

For each demographic factor (e.g., weight, age, height, and gender), an unadjusted probability of implant size ranges, such as for femoral and tibial implants, can be calculated and used for providing implant size and type recommendations. For example, a patient weighs between 60 kilograms (kg) and 70 kg. Using that information, a percentage of patients can be represented for one or more specific implant sizes in connection with recommendations made in accordance with the model for the unadjusted probability. For example, one or more processors (e.g., configured in device 102 and/or 104) execute programming instructions to determine and report that 33% of patients with weight between 60 kg and <70 kg are recommended for femoral implant size range<55 millimeters (mm).

Further, a posterior probability of implant size ranges (e.g., for femoral and tibial) can be determined using a calculated likelihood of a patient with a given profile of gender, weight, and height categories. As noted herein, data can be categorized by implant manufacturer and other factors, such as size of the femoral and tibial component, using data from a registry and individual chart review. A Bayesian model is discovered to provide substantial improvements, including increases in accuracy, and can be used to determine various probabilities, such as the posterior probability, and for recommending a respective implant size.

In one or more implementations of the present disclosure, an institutional joint replacement registry is accessed that includes information associated with patients who underwent arthroplasty (e.g., primary TKA) over a period of time, such as ten years. Implant data can be categorized by implant manufacturer and size of respective component, e.g., femoral and tibial components, using data from the registry and individual chart review. Moreover, one or more computing devices (e.g., 102 and/or 104) can access one or more data sources containing implant manufacturers' technical guides to obtain implant descriptions and implant size dimensions therefrom. In addition, patient demographics including patient age, gender, height, weight, and body mass index (BMI) can be obtained from various data sources, including a patient registry, electronic medical records, patient charts, and other data sources. Thereafter, implant sizes can then be normalized, e.g., converted, into different dimensions, for each respective manufacturer to allow for comparison across different manufacturers' designs. For example, femoral and tibial implant sizes can be converted to anteroposterior (AP) dimensions (e.g., mm) for femoral components and mediolateral (ML) dimensions (e.g., mm) for tibial components. Such dimensions can be chosen on the basis how implants typically increase in size on the femoral and tibial side, respectively, and can be chosen to simplify predictive models.

In one non-limiting example, 8,100 previously performed primary total knee arthroplasty procedures are analyzed. See Table 1, below. The mean patient age is 67.3 years (standard deviation (SD) 9.5) with a mean BMI of 30.4 kg/m 2 (SD 6.3). Further, 3,000 (approximately 37%) males are included in the cohort, of which 7,640 (approximately 96%) had a primary diagnosis of osteoarthritis. Nine major implant manufacturers' designs include: VANGUARD: 246 (approximately 3.0%); NEXGEN: 892 (approximately 11%); NEXGEN GENDER SPECIFIC: 44 (approximately 0.54%); PERSONA: 77 (approximately 0.95%); SIGMA: 382 (approximately 4.7%); OPTETRAK LOGIC: 2,789 (approximately 34.4%); JOURNEY: 434 (approximately 5.4%); LEGION: 3,071 (approximately 37.9%); TRIATHLON: 146 (approximately 1.8%); and other implant manufacturers: 19 (approximately 0.23%). The majority of the 8,100 cases were posterior stabilized (6,309, approximately 78%). Only 94 (approximately 1.2%) were cruciate retaining (CR) and 1,056 (approximately 13%) received a mid-level constrained insert while 505 (approximately 6.2%) received a constrained condylar knee (CCK) level constrained insert. Insert details for a small number, 136 (approximately 1.6%) were not available.

TABLE I

Baseline demographics end implant details.

| Variable (n = 8,100) | Total |
|---|---|
| Mean age, yrs (SD) | 67.3 (9.5) |
| Mean BMI, kg/m² (SD) | 30.4 (6.3) |
| Mean height, cm (SD) | 167.8 (10.7) |
| Mean weight, kg (SD) | 85.8 (19.9) |
| Mean femoral ML dimension, mm (SD) | 69.0 (5.4) |
| Mean femoral AP dimension, mm (SD) | 63.5 (4.7) |
| Mean tibial ML dimension, mm (SD) | 72.0 (5.2) |
| Mean tibial AP dimension, mm (SD) | 48.4 (3.7) |
| Sex, n (%) | |
| Male | 3,000 (37.04) |
| Female | 5,100 (62.96) |
| Side, n (%) | |
| Right | 4.164 (51.4) |
| Left | 3,936 (48.6) |
| Primary diagnosis, n (%) | |
| Non-OA | 460 (3.62) |
| OA | 7,640 (96.38) |
| Primary diagnosis,* n (%) | |
| OA | 7,640 (96.38) |
| AVM | 13 (0.16) |
| Inflammatory arthritis (RA, AS, SLE) | 59 (0.74) |
| PTA | 133 (1.58) |
| Others | 82 (1.03) |

*Data missing for 173 patterns.
AP, anteroposterior; AS, ankylosing spondylitis; AVN, avascular necrosis; BMI, body mass index; ML, mediolateral; OA, osteoarthritis; PTA, post-traumatic arthritis; RA, rheumatoid arthritis; SLE, systemic lupus erythematosus.

Continuing with the present example, continuous variables can be presented as mean with SDs and compared using one-way analysis of variance (ANOVA). Categorical variables can be presented as frequencies and percentages and compared using the chi-squared test, as known in the art. Moreover, Pearson correlation coefficients (ρ) and 95% confidence intervals (CIs) can assess the relationship between implant size and patient height, and between implant size and patient weight. The TKAs can be randomly split into a training cohort (4,022 TKAs) and a testing cohort (4,078 TKAs). Random splitting of the data can be performed using SAS software using simple random sampling. Thereafter, multivariate linear regression can be performed using patient height, weight, and gender on the training cohort and this formula used on the testing cohort to determine the accuracy of the model across a range of implant size tolerances.

Continuing with the present example, for each of the demographic factors (e.g., weight, height, and gender), an unadjusted probability of recommending femoral and tibial implant size range can be calculated in the training cohort. For patients with weight between 60 kg and <70 kg, the proportion of patients for whom the model would recommend a specific femoral implant size represents the unadjusted probability. For example, 33% of patients with weight between 60 kg and <70 kg were recommended for femoral implant size range <55 mm, 29% for 55 mm to <59 mm, 20% for 59 mm to <63 mm, 9% for 63 mm to <67 mm, 3% for 67 mm to <71 mm, and 1% for 71 mm to <75 mm. Moreover, the posterior probability of recommending femoral and tibial implant size range in mm can then be calculated using the likelihood of a patient with the given profile of gender, weight, and height categories in the training cohort. For example, a male patient with weight between 60 kg and <70 kg and height between 180 cm and <185 cm, the probabilities of recommending femoral implant size 55 mm to <59 mm is 0.1%, 59 mm to <63 mm is 6.6%, 63 mm to <67 mm is 62.6%, 67 mm to <71 mm is 25.1%, and 71 mm to <75 mm is 5.7%.

Continuing with the present example, the model can be applied to the testing cohort to determine the accuracy of the model, at 1%, 5%, and 10% tolerance of inaccuracy. For example, with 5% tolerance of inaccuracy, in the same scenario described above (male, 60 kg to <70 kg, and 180 cm to <185 cm), only 59 mm to <63 mm, 63 mm to <67 mm, 67 mm to <71 mm, and 71 mm to <75 mm femoral implant sizes were required (55 mm to <59 mm has 0.1%, which is less than the 5% threshold). A review of the testing cohort reveals two patients fall in the 63 mm to <67 mm and no patients fall outside the prepared implant size range. Overall, 230 patients fall outside the prepared femoral implant size range (5.6%) and 140 patients for tibial implant size range (3.4%).

Continuing with the present example, seven categories with equal intervals can be used for implant sizes, based on common differences in sizes in AP and ML dimensions of femoral and tibial components respectively across manufacturers. Weight with 10 kg intervals and height with 5 cm intervals can be used for their categories. Statistical significance can be defined by a p-value <0.05, and data analyses performed using SAS.

Continuing with the present example, the following results regard the relationship of individual demographic variables and implant size. Height has a relatively high strength correlation with implant size (femur AP: $\rho=0.73$, $p<0.001$; tibia ML: $\rho=0.77$, $p<0.001$). Weight has a moderate strength correlation with implant size (femur AP: $\rho=0.46$, $p<0.001$; tibia ML: $\rho=0.48$, $p<0.001$). BMI has a negligible correlation with implant size $\rho=0.06$ for both femur AP and tibia ML). Patient gender can have significant correlations with implant size, but not with obesity and implant size.

Figure 3:
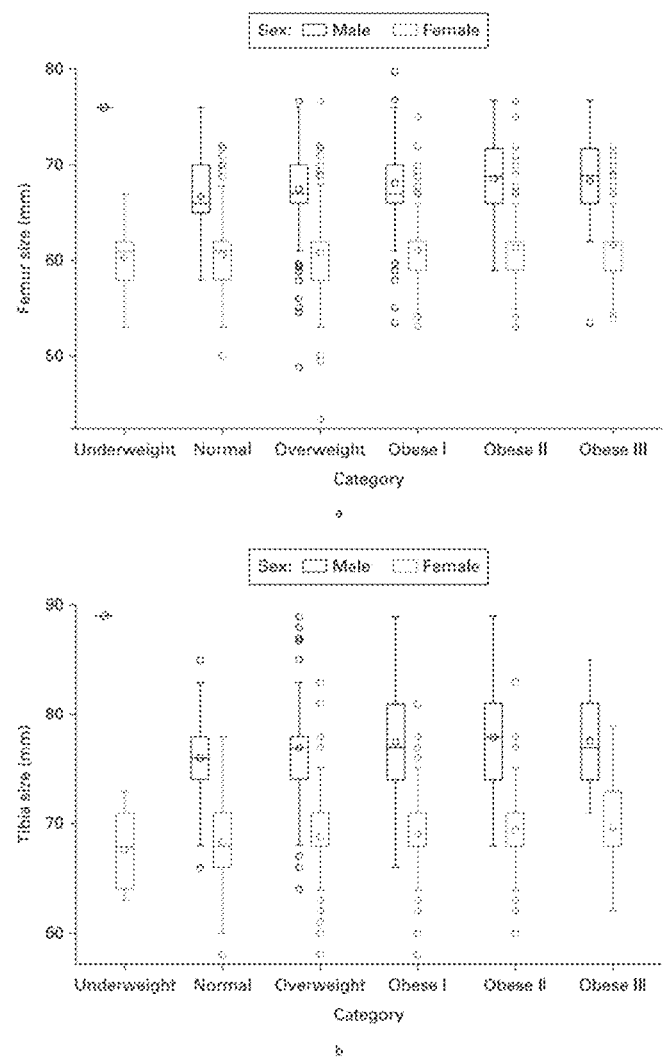
FIG. 3 illustrates an example boxplot showing a distribution of femoral and tibial implant sizes, in accordance with an example implementation of the present disclosure.

FIG. 3 illustrates an example boxplot (also referred to as box and whisker plots) showing the distribution of a) femoral (AP) and b) tibial (ML) implant sizes based on World Health Organization (BMI) categories. The female and male cohorts had no correlation with BMI. There was a significant difference in implant sizes between females and males ($p<0.001$). Boxes of the first quartile (25th percentile, bottom of the box), median (50th percentile, line inside the box), and third quartile (75th percentile, top of the box). The whiskers extend to the most extreme observations within 1.5 times the interquartile range below and above the first and third quartiles, respectively. The circle inside a box indicates the mean and the circles outside a box represent the outliers.

Continuing with the above example, a multivariate logistic regression model can be used for demographic variables including height, weight, and gender, which results in a predicted femoral AP size (mm)=31.66+0.19 height (cm)+0.03 weight (kg)−3.37 female, ($R^2=0.607$). Further, use of a multivariate logistic regression model results in predicted tibial ML size (mm)=39.59+0.19 height (cm)+0.03 weight (kg)−4.7 female ($R^2=0.695$). See, for example, Table II, below.

TABLE II

Multivariate linear regression analysis of demographic variables.

| Variable | Coefficient | p-value |
|---|---|---|
| Femur AP (mm) | | $R^2 = 0.607$ |
| Intercept | 31.66 | <0.001 |

TABLE II-continued

Multivariate linear regression analysis of demographic variables.

| Variable | Coefficient | p-value |
|---|---|---|
| Height, cm | 0.19 | <0.001 |
| Weight, kg | 0.03 | <0.001 |
| Female | −3.37 | <0.001 |
| Tibia ML (mm) | | $R^2 = 0.695$ |
| Intercept | 39.58 | <0.001 |
| Height (cm) | 0.19 | <0.001 |
| Weight (kg) | 0.03 | <0.001 |
| Female | −4.70 | <0.001 |

AP, anteroposterior; ML, mediolateral.

Moreover, the multivariate logistic regression model can then be applied to the testing cohort, and accuracy of predicting implant size for the femur±4 mm is 81.9% and for predicting size within ±5 mm is 90.7%. Accuracy of the model for predicting tibial size±4 mm is 82.3% and for predicting size within ±5 mm is 91.3%. See, for example, Table III, below.

TABLE III

Accuracy of multivariate linear regression model on testing cohort.

| Dimension and tolerance | Total, n | Accuracy, % |
|---|---|---|
| Femur AP dimension | | |
| ±1 mm | 1,055 | 25.9 |
| ±2 mm | 2,099 | 51.5 |
| ±3 mm | 2,829 | 69.4 |
| ±4 mm | 3,339 | 81.9 |
| ±5 mm | 3,698 | 90.7 |
| ±6 mm | 3,882 | 95.2 |
| ±7 mm | 3,968 | 97.3 |
| ±8 mm | 4,032 | 98.9 |
| Tibia ML dimension | | |
| ±1 mm | 1,132 | 27.8 |
| ±2 mm | 2,090 | 51.3 |
| ±3 mm | 2,848 | 69.8 |
| ±4 mm | 3,357 | 82.3 |
| ±5 mm | 3,724 | 91.3 |
| ±6 mm | 3,926 | 96.3 |
| ±7 mm | 4,008 | 98.3 |
| ±8 mm | 4,045 | 99.2 |

AP, anteroposterior; ML, mediolateral.

Figure 4A:
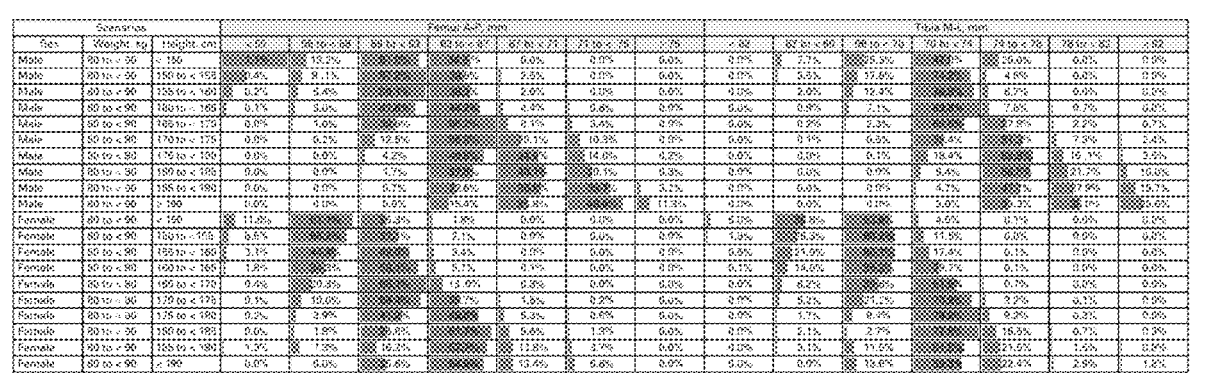

Continuing with the above example, unadjusted probabilities can be calculated for implant sizes based on three factors: height, weight, and gender. Thereafter, a Bayesian model can be used with regard to prior distributions, including to determine the posterior probability of recommending implant sizes based on these three factors. FIG. 4A illustrates example results of a testing dataset and represents the accuracy of the Bayesian model for predicting femoral and tibial component implant size. Using the testing dataset, the accuracy of the Bayesian model for predicting implant size with a tolerance of 5% inaccuracy is 94.4% for the femur and 96.6% for the tibia. When tolerance for inaccuracy was adjusted to 1%, the model is 98% accurate in predicting femoral size range and 98.7% accurate in predicting tibial size range. FIG. 4B illustrates example results of a testing dataset and represents the accuracy of a statistical model for predicting femoral stem component implant size. FIG. 4C illustrates example results of a testing dataset and represents the accuracy of a statistical model for predicting acetabular component implant size. FIG. 4D illustrates example results of a testing dataset and represents the accuracy of a statistical model for predicting acetabular cup outer diameter ("OD") size in millimeters, in connection with respective scenarios (e.g., gender, weight, and height).

Figure 5:
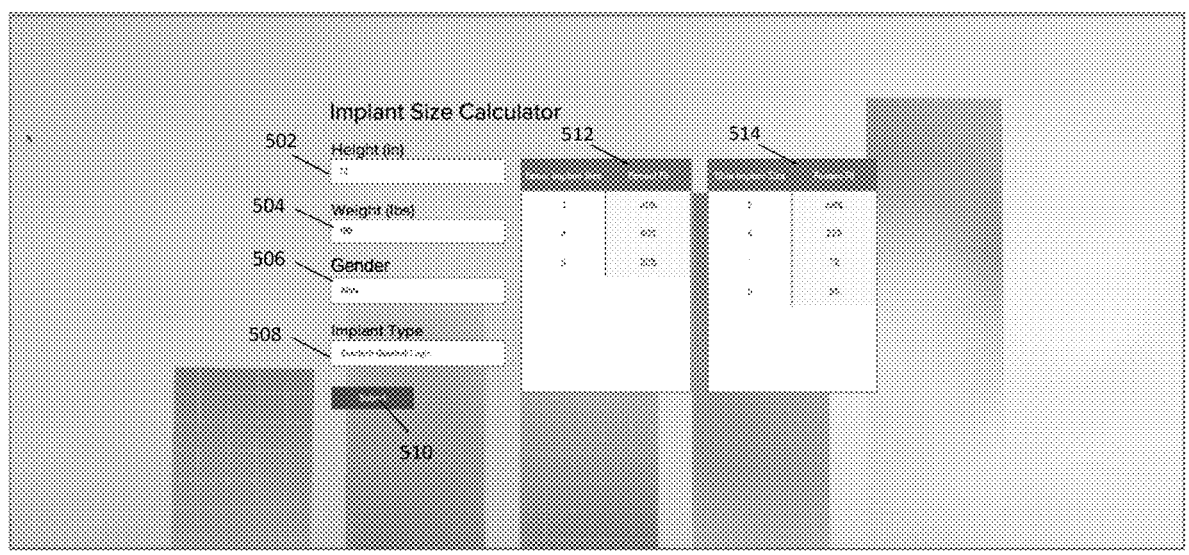
FIG. 5 illustrates an example data entry display screen that can be provided on one or more computing devices in connection with an example implementation of the present disclosure.

FIG. 5 illustrates an example data entry display screen that can be provided on one or more computing devices (e.g., devices 102 and/or 104) in connection with an example implementation of the present disclosure. In the example shown in FIG. 5, a series of graphical screen controls are provided for users to submit information that can be used to provide implant sizes and percentages of patients in which the respective implant size successfully fit. For example, height information (e.g., 72 inches) is submitted in text box control 502. Further, weight information (180 pounds) is submitted in text box control 504. Gender information (male) is submitted in text box control 506. In addition to the three demographic factors shown in FIG. 5, a graphical screen control 508 is provided for a user to identify a respective implant type. Graphical screen control 508 can be formatted as a text box, drop-down list, or other suitable tool for a user to identify a respective implant type. Providing a drop-down list or other selectable control for manufacturers' respective implant types is useful and supports users to quickly identify preferred manufacturers and implant types for each of a plurality of caregivers, such as surgeons. In the example shown in FIG. 5, an EXACTECH OPTETRAK LOGIC implant type has been selected. Of course, one of ordinary skill will recognize that other graphical screen controls can be provided to receive information regarding a respective patient, such as age, BMI, or other suitable demographic factor.

Continuing with reference to the example implementation shown in FIG. 5, after the user has submitted information for entry, the user presses submit button control 510. Using the information received, instructions are executed by a processor operating in computing device 102 and/or 104 to generate results, such as shown in tables 512 and 514. In the example shown in FIG. 5 in connection with the respective entries and selections made, three femur implant sizes (sizes 3, 4, and 5) and corresponding fit percentages (40%, 40%, and 20%) are displayed. Moreover, for respective tibia implant sizes are also displayed in table 514, including 3, 4, 5, and 6. These automatically generated values are based in accordance with the information assessed in accordance with previous procedures and statistical modeling shown and described herein.

Thus, as shown and described herein, predicting implant size, including for femoral and tibial components, can be based on readily available preoperative demographic variables and generated substantially automatically in response to patient demographic variables in the selection of implant type. In one or more implementations of the present disclosure, the entries provided in tables 512 and/or 514 are selectable for additional functionality. For example, after a selection is made by a user for a femur size 5 and a tibia size 5, computing device 102 and/or 104 interfaces with one or more other computing devices to transmit information associated with the respective selections. For example, use of one or more application programming interfaces (APIs) enable computing device 104 to submit respective implant size selections to an inventory control system. Once received, the inventory control system can generate orders for the respective implants for a forthcoming arthroplasty. Moreover, one or more APIs can be accessed by computing device 102 and/or 104 to interface with one or more computing devices associated with storage management, e-commerce, or other technology associated with a practice. Thus, the present disclosure includes interactivity within and between various intra-practice computing systems, interpractice computing systems, and third-party computing systems in connection with medical practice management and associated functionality.

The present disclosure determines a relationship between height, weight, and gender with implant size and predictions therefor, for example, in TKA, and applies a multivariate linear regression model for predicting implant size based on these variables and/or applies a Bayesian model for predicting implant size using these same variables. As noted herein, a significant relationship has been determined in accordance with the teachings herein between height and implant size (femur AP: $\rho=0.73$, $p<0.001$; tibia ML: $\rho=0.77$, $p<0.001$). Moreover, a significant correlation has been determined in accordance with the teachings herein between weight and implant size (femur AP: $\rho=0.46$, $p<0.001$; tibia ML: $\rho=0.48$, $p<0.001$). Interestingly and contrary to anecdotal observations, the systems and methods of the present disclosure did not result in a determination of significant correlations with implant size and obesity or when obesity and female gender were analyzed together (in which obese females may otherwise be predicted to require small sized components). Instead, the teachings herein result in a determination that factoring a patient's height at least in addition to or otherwise in place of weight results in more accurate implant size predictions.

Further as shown and described herein, a multivariate linear regression model that factors patient height, weight, and gender provides for accurate implant size predictions across a plurality of manufacturers. While application of the multivariate linear regression model for predicting an implant size within a certain size has been shown to be useful, outliers based on respective demographic variables and across a range of implant sizes can exist.

Accordingly, the present disclosure applies a model developed using Bayesian statistics in addition to or in place of the multivariate linear regression model. The Bayesian model provides for accurate implant predictions across a range of implant sizes that may be required for respective combinations of patient height, gender, and weight. For example, one such combination may result in a prediction based on a Bayesian statistical model that three implant respective sizes be available for femoral and tibial components, while another such combination may result in a prediction based on the Bayesian statistical model that six implant sizes be available based on the heterogeneity of implant sizes that have been required in specific patients. The present disclosure determines that the Bayesian model has a high accuracy in predicting all sizes required for each of a plurality of combinations of respective demographic factors (e.g., height, gender, and weight). For example, and accepting a 5% risk of inaccuracy (e.g., implant information being not available), a 94.4% accuracy in predicting femoral size in the AP dimension and 96.6% accuracy for predicting tibial size in the ML dimension resulted in application of the Bayesian model. Further, given acceptance of a 1% intolerance (e.g., 99% of the time, implants would be available for every combination of these demographic variables), a 98% accuracy is determined in predicting femoral AP dimension size range and 98.7% accuracy in predicting tibial ML size range when the Bayesian model is applied.

It is recognized herein that predicting implant size benefits screening practices for possible use of small sized implants in patients with known obesity. The present disclosure notes the relationship of obesity and increased stresses on tibial components in TKA, as well as obesity being an independent risk factor for aseptic loosening of the tibia. The correlation between smaller implant size and increased risk of failure of tibial components in obese patients is also recognized herein. Consideration of additional fixation has been suggested in the art to help mitigate risk of early failure, including varus tibial collapse in obese patients when small tibial components have been used. The present disclosure increases accuracy in predicting such risks for early failure using patient demographic factors beyond BMI, and preoperatively identifies those patients that will require a small implant. In connection therewith, the use of a stem may be considered in advance instead of making intraoperative changes in treatment requiring opening additional trays that may not have been prepared, or even worse, requiring stemmed implants that may not be available.

Accordingly, the present disclosure concludes that predicting implant size accurately can be related to basic demographic variables including height, weight, and gender, and BMI per se does not have a significant correlation with accurate implant size prediction. Application of both the linear regression and Bayesian models described herein accurately predict implant sizes across multiple manufacturers based on height, weight, and gender alone. Application of the Bayesian modeling can be more useful to determine a range of required implant sizes for each scenario. Benefits of increases in implant size predictions can include medical improvements directly resulting from implant size selections, as well increases in operating room and implant supply chain efficiency and corresponding cost savings associated with inventory control, shipping, and storage management.

In addition to accurate implant size recommendations generated as a function of patient demographic factors, the present disclosure can further include an algorithm to determine, via one or more matching processes, one respective implant size for each respective manufacturer. For example, an algorithm can be defined and utilized by one or more processors (e.g., configured in device 102 and/or 104) to match a given Bayesian range of knee dimensions in anterior-posterior or mediolateral millimeters to one femoral and/or one tibial implant size per manufacturer. Graphical screen controls can be provided in one or more user interfaces for users to submit information that can be used to provide implant sizes and percentages of patients in which the respective implant size successfully fit (FIG. 5).

In one or more implementations of the present disclosure, such size and percentage values can further be combined with other data, such as data that are publicly accessible, to correlate the predicted dimensions with implant sizes provided by a respective manufacturer (e.g., knee implant sizes). For example, a prediction can be made that a female patient with a height of 190 centimeters and a weight of 80 kilograms has a 60% chance of having a right knee with a femoral anterior-posterior dimension between 65 and 69 millimeters. Thereafter, a search can be conducted of one or more databases (e.g., including publicly accessible databases) to relate femoral dimensions to femoral implant sizes, per manufacturer. The results of the search can include a respective femoral implant size for a respective manufacturer. Continuing with the previous example, the range of 65 to 69 millimeters can correlate to a femoral implant provided by a respective manufacturer (e.g., EXACTECH OPTETRAK LOGIC) and having a size of 3. Moreover, the process can repeat to identify an implant and corresponding size for a tibial implant. Accordingly, a patient's demographic variables can be used to identify a set of dimension ranges (e.g., knee dimension ranges) that each correlate to a specific percentage likelihood of accuracy, and each of dimension ranges (e.g., knee dimension ranges) can be respectively related to one unique implant size for each manufacturer.

The search and identification process described above has some limitations due to information in two or more respective databases that do not have a one-to-one mapping to a respective range, which results in missing or inaccurate records being retrieved. Such inaccuracy can be attributed to various causes. For example, one range (e.g., 65 to 69 millimeters) of knee dimensions based on a Bayesian model (referred to herein, generally, as a "Bayesian range") maps to two or more respective implant sizes provided by a given manufacturer (e.g., STRYKER). In another example, one Bayesian range (e.g., 65 to 69 millimeters) maps to no knee implant sizes for a given manufacturer.

The present disclosure addresses and resolves such shortcomings via an algorithm (referred to herein, generally, as a "matching algorithm") that, when applied by one or more processors, provides search results for respective implant sizes. More particularly, the matching algorithm ensures that each knee dimension range calculated via a Bayesian model maps to exactly one unique implant size per manufacturer, for example, for femoral and tibial sizes and implants.

Below is a table showing features of a matching algorithm process in accordance with an example implementation.

Matching Algorithm Process

This example includes Femur implant sizes only, but can be used to calculate tibia implant size

| Output of Bayesian Model: Set of Percent Fit Likelihood to Femur Size Bayesian Range | | Public Dataset for a Given Manufacturer: Femur Size to Femur Implant Size | | Raw Match between Percent Fit Likelihood and Femur Implant Size | | Cleaned Match between Percent Fit Likelihood and Femur Implant Size | |
|---|---|---|---|---|---|---|---|
| Percent Fit Likelihood (%) | Femur Size Bayesian Range (mm) | Femur Size (mm) | Femur Implant Size | Percent Fit Likelihood (%) | Femur Implant Size | Percent Fit Likelihood (%) | Femur Implant Size |
| 30 | 61-65 | 61 | 1 | 30 | 1, 2 | 15 | 1 |
| 40 | 65-69 | 64 | 2 | 40 | 3 | 15 | 2 |
| 20 | 69-73 | 68 | 3 | 20 | 4 | 40 | 3 |
| 10 | 73-77 | 72 | 4 | 10 | N/A | 30 | 4 |

The matching algorithm is now described with regard to (1) patient demographic variables to femoral and tibial dimension Bayesian ranges, and (2) femoral and tibial dimensions to femoral and tibial implant sizes per manufacturer. As used herein, the term "knee size," generally, refers to femur and tibia size. In one or more implementations, for any given knee size, a respective Bayesian range includes a value representing a lower bound but excludes the upper bound. Excluding the upper bound of the range is useful to avoid duplicative results. For example, a range of 65 to 69 millimeters would include 65 millimeters but not 69 millimeters. Moreover, any outputted knee size having a range that is within less than a 1% fit likelihood is ignored. This ensures that the summed percentage likelihoods will be 99-100% inclusive. Furthermore, in one or more implementations of the present disclosure, each percentage likelihood fit is rounded to a whole number. In one or more implementations of the present disclosure, these parameters are included during processes that apply the matching algorithm.

Figure 6:
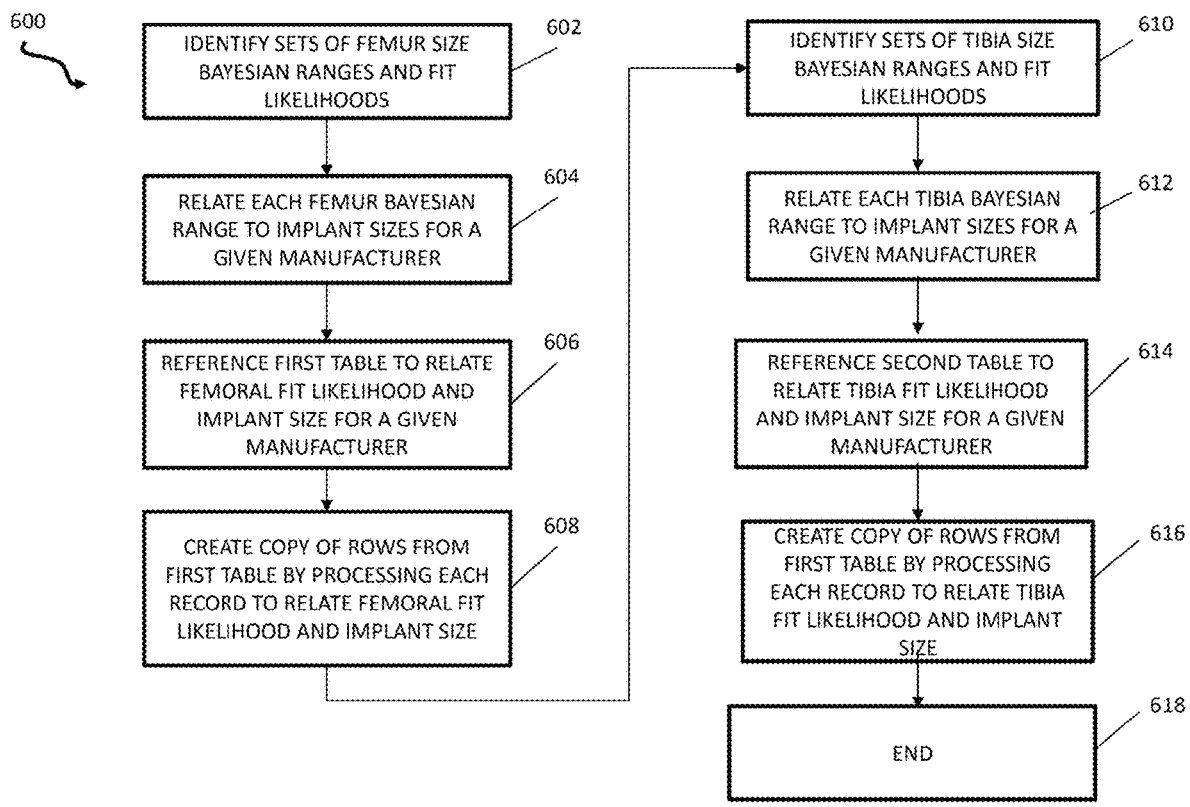
FIG. 6 is a flowchart illustrating steps associated with a matching algorithm in connection with an example implementation of the present disclosure for femur and tibia size Bayesian ranges.

FIG. 6 is a flowchart illustrating steps 600 associated with a matching algorithm in connection with an example implementation of the present disclosure for femur and tibia size Bayesian ranges. At step 602, sets of femur size Bayesian ranges and corresponding percentage fit likelihoods that relate to a given patient's demographic variables are identified. For example, a female patient who weighs 80 kilograms and is 190 centimeters tall is determined to have a 30% likelihood of having a femur between 61 and 65 millimeters anterior-posterior. Thereafter, each femur size Bayesian range is related to all femur implant sizes for a respective manufacturer (step 604). For example, a femoral implant of size 2 may fit a femur with anterior-posterior dimensions of 61 to 65 millimeters anterior-posterior.

Continuing with reference to the flow chart in FIG. 6, a table containing femoral implant sizes for a respective manufacturer is referenced to be updated to relate percentage fit likelihoods (step 606). Each row in the table is processed to identify a respective femoral implant size from the manufacturer for each row in the table related percentage fit likelihoods (step 608). A similar process occurs for tibia implants. In one or more implementations, a table maps patient demographic variables to Bayesian ranges and fit likelihoods for both femur and tibia, is static and is not updated. Two copies of a given row in the table can be created for both femur and tibia, respectively, and that each relates respective demographic variables. The copies are modified, such as in accordance with algorithmic steps shown and described herein (e.g., in FIGS. 7 and 8). These copies can contain the implant sizes and fit likelihoods that are displayed, such as in the example user interface illustrated in FIG. 5. This can be done for both femoral and tibial sizes and components.

Continuing with reference to the flow chart in FIG. 6, at step 610, sets of tibia size Bayesian ranges and corresponding percentage fit likelihoods that relate to a given patient's demographic variables are identified. Thereafter, each tibia size Bayesian range is related to all tibia implant sizes for a given manufacturer (step 612). A table containing tibia implant sizes for a respective manufacturer is referenced to be updated to relate percentage fit likelihoods (step 614). Each row in the table is processed to identify a respective tibia implant size from the manufacturer for each row in the table related percentage fit likelihoods (step 616). Thereafter, the process ends at step 618.

Figure 7:
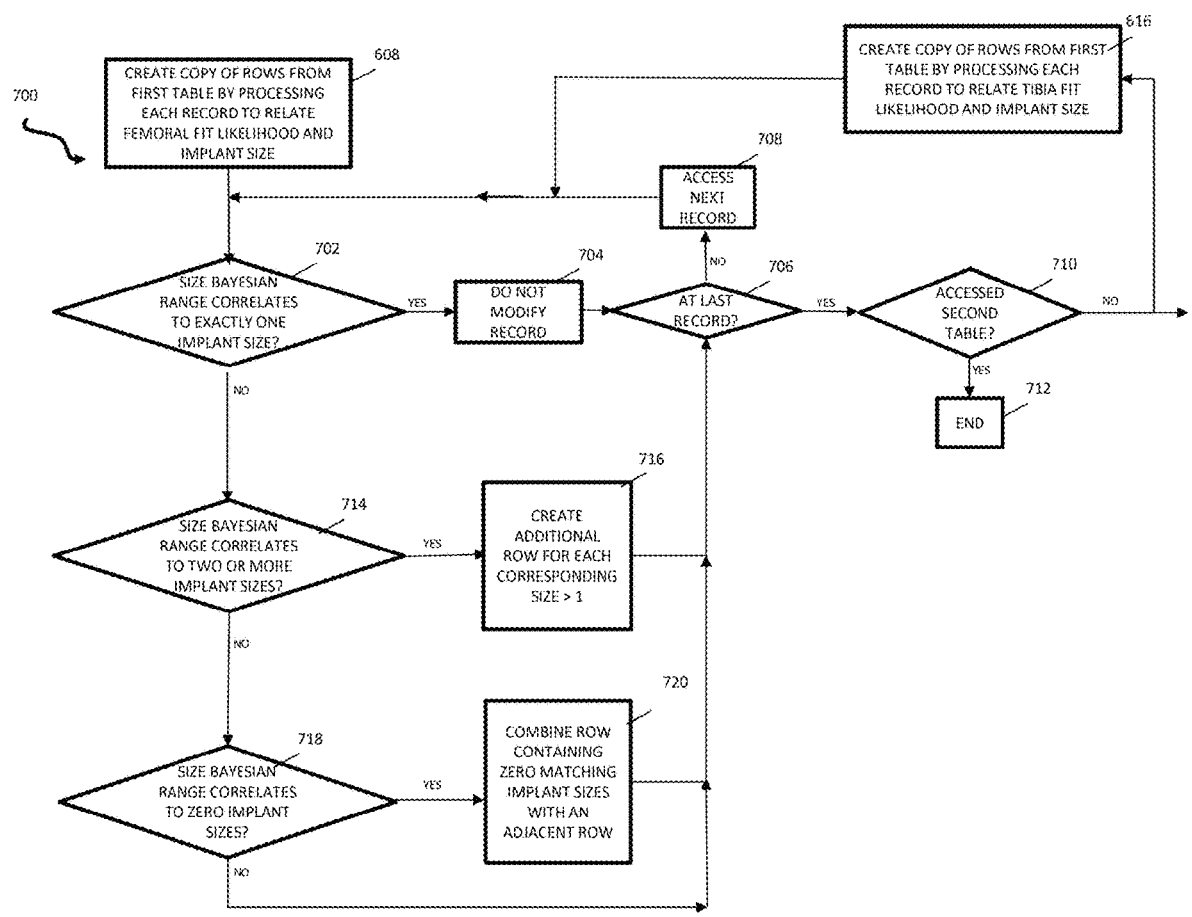
FIG. 7 is a flowchart illustrating steps associated with additional details in connection with the matching algorithm of FIG. 6.

FIG. 7 is a flowchart illustrating steps 700 associated with additional details in connection with the matching algorithm of FIG. 6, in connection with an example implementation of the present disclosure for femur and tibia size Bayesian ranges. At step 702, a determination is made whether a respective femoral size Bayesian range in accordance with a respective row in the first or second table correlates to exactly one femoral implant size for the given manufacturer, as identified in step 604. If the determination at step 702 is in the affirmative, then the process branches to step 704 and the row is not modified. In other words, there is a direct match for the respective femoral size Bayesian range (e.g., between 61 and 65 millimeters anterior-posterior to a respective manufacturer's implant. Continuing from step 704, thereafter, the process continues to step 706 and a determination is made whether the current record being processed is the last record in the table (e.g., the first table or the second table, depending on which table is being processed). If the determination at step 706 is negative (i.e., not the last record in the table is being processed), then the process branches to step 708 and the next record is accessed. Thereafter, the process continues back to step 702. In the alternative, if the determination at step 706 is affirmative (i.e., the last record in the table was processed), then the process branches to step 710 and a determination is made whether the second table (as in step 616) has been accessed. If the determination at step 710 is negative (i.e., the second table has not been accessed), then the process branches to step 616, and the second table is accessed and updated by processing each record to relate tibia fit likelihood and implant size. The process continues from step 616 to step 702. Alternatively, if the determination at step 710 is affirmative, then the process ends at step 712.

Continuing with reference to FIG. 7, if the determination at step 702 is negative, then the process branches to step 714 and a determination is made whether a given femoral size Bayesian range correlates to two or more femoral implant sizes for a given manufacturer. If the determination at step 714 is affirmative, then the process branches to step 716 and one additional row is created for each corresponding size greater than one, for a femoral or tibia (depending on which table is being processed). These size(s) are then placed accordingly. In one or more implementations, the original percentage fit likelihood is divided evenly by the number of corresponding femoral sizes, and each row will contain a new percentage fit likelihood for each respective implant size. For example, the femoral size Bayesian range of 61-65 millimeters anterior-posterior may have a percentage fit likelihood of 30%, which maps to both size 2 and size 3 by a given manufacturer. As such, one additional row is created, totaling two rows for this femoral Bayesian range. One row has a percentage fit likelihood of 15% and a femoral implant size of 2, and the second row has a percentage fit likelihood of 15% and a femoral implant size of 3.

Continuing from step 716, the process continues to step 706 and a determination is made whether the current record being processed is the last record in the table (e.g., the first table or the second table, depending on which table is being processed). If the determination at step 706 is negative (i.e., not the last record in the table is being processed), then the process branches to step 708 and the next record is accessed for processing. Thereafter, the process continues back to step 702. In the alternative, if the determination at step 706 is affirmative (i.e., the last record in the table was processed), then the process branches to step 710 and a determination is made whether the second table (as in step 616) has been accessed. If the determination at step 710 is negative (i.e., the second table has not been accessed), then the process branches to step 616, and the second table is accessed and updated by processing each record to relate tibia fit likelihood and implant size. The process continues from step 616 to step 702. Alternatively, if the determination at step 710 is affirmative, then the process ends at step 712.

Continuing with reference to FIG. 7, if the determination at step 714 is negative, then the process branches to step 718 and a determination is made whether a given femoral size Bayesian range correlates to zero femoral or tibia (depending on the state of the process) implant sizes for a given manufacturer. If the determination at step 718 is affirmative, then the process branches to step 720 and the row containing zero matching implant sizes is combined with an adjacent row. This process is repeated until the adjacent row has at least one corresponding implant size. As used herein the term "combine" refers, generally, to expand the femoral or tibia size Bayesian range of the original row to include the femoral or tibia size Bayesian range of the adjacent row. The effect of this modification is that (1) the original row is removed from the table, and (2) the percentage fit likelihood is added to that of the adjacent row below. If this case applies to the last row in the table, then the adjacent row above is used instead. For example, the femoral size Bayesian range of 61-65 millimeters anterior-posterior has a percentage fit likelihood of 30% and maps to zero femoral implant sizes for a given manufacturer. Moreover, the femoral size Bayesian range of 65-69 millimeters anterior-posterior has a percentage fit likelihood of 20% and maps to a femoral implant of size 2 for the same given manufacturer. The former row would be removed from the table, with the latter row having a percentage likelihood fit of 50% and a size of 2.

Alternatively, if the determination at step 718 is negative, then the process branches to step 706 and a determination is made whether the current record being processed is the last record in the table (e.g., the first table or the second table, depending on which table is being processed). If the determination at step 706 is negative (i.e., not the last record in the table is being processed), then the process branches to step 708 and the next record is accessed for processing. Thereafter, the process continues back to step 702. In the alternative, if the determination at step 706 is affirmative (i.e., the last record in the table was processed), then the process branches to step 710 and a determination is made whether the second table (as in step 616) has been accessed. If the determination at step 710 is negative (i.e., the second table has not been accessed), then the process branches to step 616, and the second table is accessed and updated by processing each record to relate tibia fit likelihood and implant size. The process continues from step 616 to step 702. Alternatively, if the determination at step 710 is affirmative, then the process ends at step 712.

Although the implementation of the matching algorithm shown in FIGS. 6 and 7 and described herein includes specific features and sequences, other implementations that have slight modifications are envisioned herein, such as different Bayesian range bound settings. Notwithstanding minor variations, such modifications are supported and do not depart from the teachings of the present disclosure. For example, an alternative implementation of a matching algorithm can include one or more graphical user interfaces for a user to specify an implant manufacturer. One or more computing devices can use the specified manufacturer as a basis of filtering to output femoral and tibial implant sizes just for the specified manufacturer. In addition or in the alternative, no manufacturer can be specified (e.g., the user can leave an option for specifying an implant manufacturer blank), and the manufacturer criterion is not used for filtering, which can result in output identifying all relevant femoral and tibial implant sizes for all manufacturers that are identified in one or more databases.

In yet another example alternative implementation, an upper bound of a given femoral or tibial Bayesian range can be included, as opposed to a previously described implementation that excludes the upper bound, for example, to eliminate duplicative results. Moreover, in yet one or more other implementations of the present disclosure, the lower bound of a given femoral or tibial Bayesian range can be excluded, while the upper bound of the given femoral or tibial Bayesian range can be included. Thus, as shown and described herein, alternative implementations are supported without departing from the spirit of the disclosure.

The present disclosure provides advantages and benefits over known technology. For example, implementations of the present disclosure that include a matching algorithm improves accuracy and avoids retrieval of erroneous results. Moreover, the teachings herein provide a new way to output corresponding implant size(s) and manufacturers, even in cases where a given femoral or tibial size Bayesian range would not directly map to any implant size for a given manufacturer. Still further, in cases where all corresponding implant sizes would be output to have the same percentage fit likelihood, for example, in cases where a given femoral or tibial size Bayesian range maps to two or more implant sizes, the present disclosure automatically adjusts to ensure that all percentage fit likelihoods are not greater or lesser than 100%. The present disclosure further precludes inaccurate portrayal of actual percentage fit likelihoods for each corresponding implant size, for example, as shown and described with reference to FIGS. 6 and 7.

Yet another benefit of the present disclosure regards the ability to match femoral and tibial dimensions with corresponding implant sizes per manufacturer in a unique 1-to-1 mapping. The frequency of each of the example cases described herein are dependent upon the size of the femoral and tibial size Bayesian ranges. For example, ranges can measure 4 millimeters. If such ranges are lengthened, then there would be fewer cases where a given Bayesian range maps to zero implant sizes, but more cases where a given Bayesian range maps to more than one implant size. Alternatively, if these ranges are to be shortened, then there would be more cases where a given Bayesian range maps to zero implant sizes, but fewer cases where a given Bayesian range maps to more than one implant size. The present disclosure, including the matching algorithm, addresses each of these shortcomings by addressing ranges that would cause such undesirable results.

The present disclosure is now further described with reference to predicting implant size in total hip arthroplasty, including via predictive modeling for an acetabular component and femoral stems for a plurality of manufacturers.

The demand for total hip arthroplasty (THA) is expected to continue to grow by approximately 174% by 2030. The ability to manage resources efficiently, therefore, is becoming more difficult and important. The present disclosure evaluates the ability of linear regression and Bayesian statistics in predicting implant size for THA using patient demographic variables. In a respective study in accordance with the teachings herein, a retrospective, single institution's joint replacement registry review was performed on patients who underwent primary THA, for example, from 2010 to 2019. Demographic information including age, gender, weight, height, and body mass index (BMI) was obtained along with primary THA implant data. 11,730 acetabular and 8,536 femoral components from the most frequently used designs were included. A multivariable regression model was created on a training cohort of, for example, 80% of the sample and applied to the validation cohort (remaining 20%). Similarly, Bayesian posterior probability methods was applied to the training cohort and then tested in the validation cohort to determine the 1%, 5%, and 10% error tolerance thresholds.

With regard to results, a highly predictive regression model includes height, weight, and gender, (acetabular cup: $R^2=0.57$, all $p<0.001$; femoral stem mediolateral size [M/L]: $R^2=0.32$, all $p<0.001$). Removing weight had a minimal effect and resulted in a more parsimonious model (acetabular cup: $R^2=0.56$, all $p<0.001$; femoral stem M/L: $R^2=0.32$, all $p<0.001$). Applying the posterior probability estimate to the validation cohort using height, weight, and gender, demonstrated high accuracy in predicting the range of required implant sizes (95.3% acetabular cup and 90.4% femoral stem M/L size).

Accordingly, in accordance with the present disclosure, implant size in THA can be correlated with demographic variables including height, weight, and gender, which can be used in Bayesian modelling, as well as other models such as linear regression, to predict implant size accurately. Predictive models such as linear regression and Bayesian modelling can be used to improve operating room efficiency, supply chain inventory management, and decrease costs associated with THA.

Figure 8:
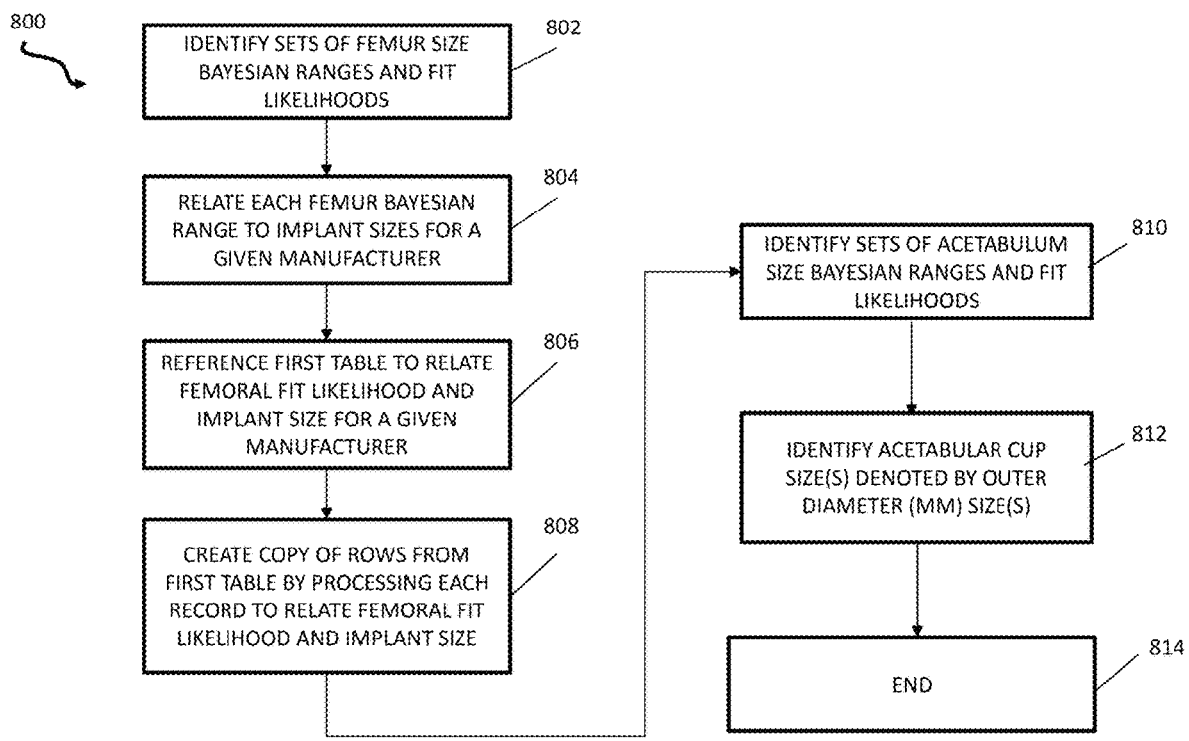
FIG. 8 is a flowchart illustrating steps associated with a matching algorithm in connection with an example implementation of the present disclosure for femur and tibia size Bayesian ranges.

FIG. 8 is a flowchart illustrating steps 800 associated with a matching algorithm in connection with an example implementation of the present disclosure for acetabular cup and femoral stem size Bayesian ranges. At step 802, sets of femur size Bayesian ranges and corresponding percentage fit likelihoods that relate to a given patient's demographic variables are identified. For example, a female patient who weighs 80 kilograms and is 190 centimeters tall is determined to have a 30% likelihood of having a femur between 61 and 65 millimeters anterior-posterior. Thereafter, each femur size Bayesian range is related to all implant sizes for a respective manufacturer (step 804).

Continuing with reference to the flow chart in FIG. 8, a table containing implant sizes for a respective manufacturer is referenced to be updated to relate percentage fit likelihoods (step 806). Each row in the table is processed to identify a respective implant size from the manufacturer for each row in the table related percentage fit likelihoods (step 808). At step 810, sets of acetabulum size Bayesian ranges and corresponding percentage fit likelihoods that relate to a given patient's demographic variables are identified. Thereafter, one or more acetabular cup sizes are identified, as denoted by cup outer diameter (OD) in mm (step 812). Thereafter, the process ends at step 814.

Figure 9:
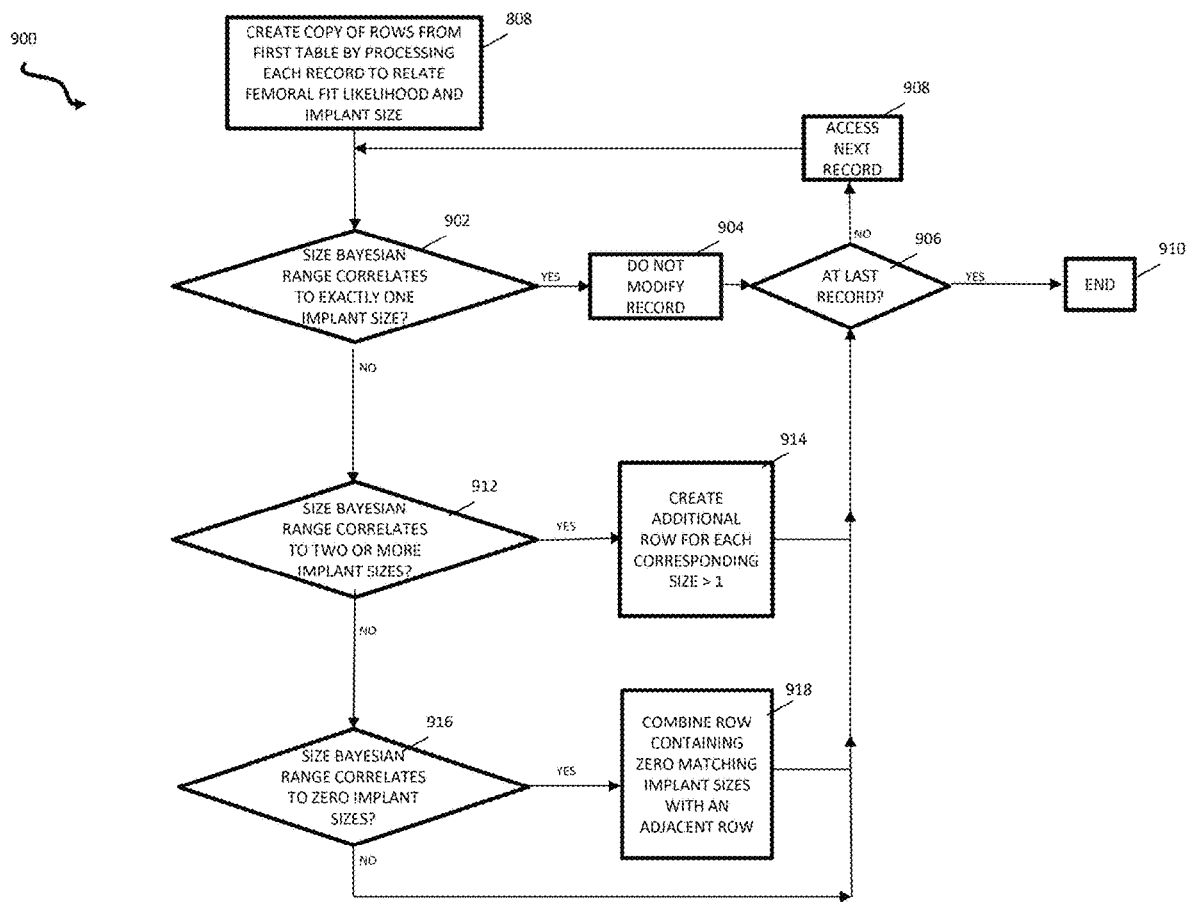
FIG. 9 is a flowchart illustrating steps associated with additional details in connection with the matching algorithm of FIG. 8.

FIG. 9 is a flowchart illustrating steps 900 associated with additional details in connection with the matching algorithm of FIG. 8, in connection with an example implementation of the present disclosure for femoral stem and acetabulum size Bayesian ranges. At step 902, a determination is made whether a respective femoral size Bayesian range in accordance with a respective row in the first or second table correlates to exactly one implant size for the given manufacturer, as identified in step 808 (FIG. 8). If the determination at step 902 is in the affirmative, then the process branches to step 904 and the row is not modified. In other words, there is a direct match for the respective femoral stem size Bayesian range (e.g., between 30 and 32 millimeters medial-lateral) to a respective manufacturer's implant. Continuing from step 904, thereafter, the process continues to step 906 and a determination is made whether the current record being processed is the last record in the table. If the determination at step 906 is negative (i.e., not the last record in the table is being processed), then the process branches to step 908 and the next record is accessed. Thereafter, the process continues back to step 902. In the alternative, if the determination at step 906 is affirmative (i.e., the last record in the table was processed), then the process branches to step 910 and the process ends.

Continuing with reference to FIG. 9, if the determination at step 902 is negative, then the process branches to step 912 and a determination is made whether a given femoral size Bayesian range correlates to two or more implant sizes for a given manufacturer. If the determination at step 912 is affirmative, then the process branches to step 914 and one additional row is created for each corresponding size greater than one. These size(s) are then placed accordingly. In one or more implementations, the original percentage fit likelihood is divided evenly by the number of corresponding femoral sizes, and each row will contain a new percentage fit likelihood for each respective implant size. For example and with reference to the first row in FIG. 4C, a male patient who weighs<50 kg and is <150 cm tall, the femoral size Bayesian range of 28-30 millimeters medial-lateral may have a percentage fit likelihood of 53.1%. Using a similar algorithm for predicting a given manufacturer's implant size in the knee, these data are available to look up the given manufacturer's implant size for the femoral stem in the hip.

Continuing from step 914, the process continues to step 906 and a determination is made whether the current record being processed is the last record in the table (e.g., the first table or the second table, depending on which table is being processed). If the determination at step 906 is negative (i.e., not the last record in the table is being processed), then the process branches to step 908 and the next record is accessed for processing. Thereafter, the process continues back to step 902. In the alternative, if the determination at step 906 is affirmative (i.e., the last record in the table was processed), then the process branches to step 910 and the process ends.

Continuing with reference to FIG. 9, if the determination at step 912 is negative, then the process branches to step 916 and a determination is made whether a given femoral size Bayesian range correlates to zero implant sizes for a given manufacturer. If the determination at step 916 is affirmative, then the process branches to step 918 and the row containing zero matching implant sizes is combined with an adjacent row. This process is repeated until the adjacent row has at least one corresponding implant size. As used herein the term "combine" refers, generally, to expand the femoral size Bayesian range of the original row to include the femoral size Bayesian range of the adjacent row. The effect of this modification is that (1) the original row is removed from the table, and (2) the percentage fit likelihood is added to that of the adjacent row below. If this case applies to the last row in the table, then the adjacent row above is used instead. For example, the femoral stem size Bayesian range of 32-34 millimeters medial-lateral for a male<50 kg and between 160-165 cm has a percentage fit likelihood of 3.5% for a given manufacturer. Moreover, the femoral stem size Bayesian range of 30-32 millimeters medial-lateral for the same patient has a percentage fit likelihood of 33.8% for the same given manufacturer. In such instance, the former row would be removed from the table, with the latter row having a percentage likelihood fit of 33.8% for 32-34 millimeters medial-lateral.

Alternatively, if the determination at step 916 is negative, then the process branches to step 906 and a determination is made whether the current record being processed is the last record in the table (e.g., the first table or the second table, depending on which table is being processed). If the determination at step 906 is negative (i.e., not the last record in the table is being processed), then the process branches to step 908 and the next record is accessed for processing. Thereafter, the process continues back to step 902. In the alternative, if the determination at step 906 is affirmative (i.e., the last record in the table was processed), then the process branches to step 910 and the process ends.

Although the implementation of the matching algorithm shown in FIGS. 8 and 9 and described herein includes specific features and sequences, other implementations that have slight modifications are envisioned herein, such as different Bayesian range bound settings. Notwithstanding minor variations, such modifications are supported and do not depart from the teachings of the present disclosure. For example, an alternative implementation of a matching algorithm can include one or more graphical user interfaces for a user to specify an implant manufacturer. One or more computing devices can use the specified manufacturer as a basis of filtering to output femoral stem and acetabular sizes just for the specified manufacturer. In addition, or in the alternative, no manufacturer can be specified (e.g., the user can leave an option for specifying an implant manufacturer blank), and the manufacturer criterion is not used for filtering, which can result in output identifying all relevant femoral stem and acetabular sizes for all manufacturers that are identified in one or more databases.

Moreover, in one or more implementations of the present disclosure, a simplified version of the matching algorithm for the acetabulum is applied since the current statistical model will always produce at least two acetabular implant sizes (e.g., in mm) for a given Bayesian range. Accordingly, such version of the matching algorithm can be used in one or more implementations of the present disclosure, except in cases where a one-to-one match between a Bayesian range, an implant size (e.g., in mm), and a manufactured implant size (e.g., "2") is guaranteed.

While operations shown and described herein may be in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this disclosure, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this disclosure have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing can be advantageous.

What is claimed is:

1. A computer-implemented method, comprising:
   receiving, by at least one processor configured by executing instructions stored on processor readable media, information associated with an upcoming arthroplasty and demographic factors of a patient in the upcoming arthroplasty;
   accessing, by the at least one processor, i) procedure information representing arthroplasty previously performed for each of a plurality of patients and ii) implant information representing types and sizes of implants from a plurality of manufacturers;
   determining, by the at least one processor, respective unadjusted probabilities of each of a plurality of implant size options within a range of implant sizes, based on i) of at least one statistical model, ii) the accessed procedure information and the implant information, and iii) the demographic factors of the patient;
   generating, by the at least one processor, information representing some of the respective implant size options and unadjusted probabilities; and
   transmitting automatically, by the at least one processor to at least one computing device associated with an inventory control system, the generated information.

2. The computer-implemented method of claim 1, wherein the inventory control system generates at least one order for at least one implant respectively associated with the some of the respective implant size options and unadjusted probabilities.

3. The computer-implemented method of claim 1, further comprising:
   using, by the at least one processor, at least one application programming interface ("API") to transmit the generated information to the at least one computing device associated with an inventory control system.

4. The computer-implemented method of claim 1, further comprising:
   using, by the at least one processor, at least one API to transmit information associated with the generated information to at least one computing device associated with shipping, storage management, or both shipping and storage management.

5. The computer-implemented method of claim 1, further comprising:
   providing, by the at least one processor, in a graphical user interface operating on at least one user computing device, information representing the respective implant size options and unadjusted probabilities; and
   receiving, via the graphical user interface, a selection of at least one of the respective implant size options and unadjusted probabilities,
   wherein generating, by the at least one processor, the information representing some of the respective implant size options and unadjusted probabilities is based at least in part on the selection received via the graphical user interface.

6. The computer-implemented method of claim 1, further comprising applying, by the at least one processor, a matching algorithm to identify one unique implant size provided by each of a plurality of manufacturers, for a respective anatomical dimension size range.

7. The computer-implemented method of claim 1, wherein the at least one statistical model is a Bayesian model.

8. The computer-implemented method of claim 7, wherein the Bayesian model includes application of:

$$P(B) = P(B \mid A_1)P(A_1) + P(B \mid A_2)P(A_2) + \cdots + P(B \mid A_n)P(A_n) = \sum_i P(B \mid A_i)P(A_i).$$

9. The computer-implemented method of claim 1, wherein the demographic factors of the patient include gender, height, and weight.

10. The computer-implemented method of claim 1, wherein the arthroplasty previously performed for each of a plurality of patients includes total knee arthroplasty or total hip arthroplasty.

11. A computer-implemented system, comprising:
    at least one computing device comprising at least one processor and a memory that includes instructions that, when executed by the at least one processor, configure the at least one processor to:
    receive information associated with an upcoming arthroplasty and demographic factors of a patient in the upcoming arthroplasty;
    access i) procedure information representing arthroplasty previously performed for each of a plurality of patients and ii) implant information representing types and sizes of implants from a plurality of manufacturers;
    determine respective unadjusted probabilities of each of a plurality of implant size options within a range of implant sizes, based on i) of at least one statistical model, ii) the accessed procedure information and the implant information, and iii) the demographic factors of the patient;
    generate information representing some of the respective implant size options and unadjusted probabilities; and
    transmit automatically to at least one computing device associated with an inventory control system, the generated information.

12. The computer-implemented system of claim 11, wherein the inventory control system generates at least one order for at least one implant respectively associated with the some of the respective implant size options and unadjusted probabilities.

13. The computer-implemented system of claim 11, wherein the at least one processor is further configured to:
    use at least one application programming interface ("API") to transmit the generated information to the at least one computing device associated with an inventory control system.

14. The computer-implemented system of claim 11, wherein the at least one processor is further configured to:
    use at least one API to transmit information associated with the generated information to at least one computing device associated with shipping, storage management, or both shipping and storage management.

15. The computer-implemented system of claim 11, wherein the at least one processor is further configured to:
provide, in a graphical user interface operating on at least one user computing device, information representing the respective implant size options and unadjusted probabilities; and
receive, via the graphical user interface, a selection of at least one of the respective implant size options and unadjusted probabilities,
wherein generating the information representing some of the respective implant size options and unadjusted probabilities is based at least in part on the selection received via the graphical user interface.

16. The computer-implemented system of claim 11, wherein the at least one processor is further configured to:
apply a matching algorithm to identify one unique implant size provided by each of a plurality of manufacturers, for a respective anatomical dimension size range.

17. The computer-implemented system of claim 11, wherein the at least one statistical model is a Bayesian model.

18. The computer-implemented system of claim 17, wherein the Bayesian model includes application of:

$$P(B) = P(B \mid A_1)P(A_1) + P(B \mid A_2)P(A_2) + \cdots + P(B \mid A_n)P(A_n) = \sum_i P(B \mid A_i)P(A_i).$$

19. The computer-implemented system of claim 11, wherein the demographic factors of the patient include gender, height, and weight.

20. The computer-implemented system of claim 11, wherein the arthroplasty previously performed for each of a plurality of patients includes total knee arthroplasty or total hip arthroplasty.

* * * * *